United States Patent [19]

Sosalla et al.

[11] Patent Number: 5,593,401
[45] Date of Patent: Jan. 14, 1997

[54] ABSORBENT ARTICLE WITH BRIDGE FLAP

[75] Inventors: Paula M. Sosalla; Yong Li; Dan D. Endres, all of Appleton, Wis.

[73] Assignee: Kimberly-Clark Corporation, Neenah, Wis.

[21] Appl. No.: 286,083

[22] Filed: Aug. 3, 1994

[51] Int. Cl.[6] .............................. A61F 13/15; A61F 13/20
[52] U.S. Cl. ................................. 604/385.2; 604/385.1; 604/387
[58] Field of Search .......................... 604/385.1, 385.2, 604/397, 390–2, 386, 387

[56] References Cited

U.S. PATENT DOCUMENTS

| | | | |
|---|---|---|---|
| 584,490 | 6/1897 | Warren . | |
| 879,774 | 2/1908 | Jonata . | |
| 1,096,477 | 5/1914 | Weisert . | |
| 1,195,904 | 8/1916 | Bornstein . | |
| 1,431,315 | 10/1922 | Le Moine . | |
| 1,676,144 | 7/1928 | Houseknecht . | |
| 2,025,843 | 12/1935 | Anderson | 128/284 |
| 2,492,265 | 12/1949 | Bryan | 128/287 |
| 2,516,951 | 8/1950 | Brink | 128/287 |
| 2,545,761 | 3/1951 | Brink | 128/287 |
| 2,564,094 | 8/1951 | Brandl | 128/284 |
| 2,566,139 | 8/1951 | Ostrovsky et al. | 128/284 |
| 2,739,594 | 3/1956 | Baten | 128/284 |
| 2,830,589 | 4/1958 | Doner | 128/284 |
| 2,832,345 | 4/1958 | Webb . | |

(List continued on next page.)

FOREIGN PATENT DOCUMENTS

| | | | |
|---|---|---|---|
| 0059015B1 | 9/1982 | European Pat. Off. . | |
| 0059014B1 | 9/1982 | European Pat. Off. . | |
| 0217032A3 | 4/1987 | European Pat. Off. . | |
| 0252413B1 | 1/1988 | European Pat. Off. . | |
| 0264238 | 4/1988 | European Pat. Off. . | |
| 0339461B1 | 11/1989 | European Pat. Off. . | |
| 0376022 | 7/1990 | European Pat. Off. . | |
| 0404648A1 | 12/1990 | European Pat. Off. . | |
| 0487758A1 | 6/1992 | European Pat. Off. . | |
| 0508477 | 10/1992 | European Pat. Off. . | |
| 0528282A2 | 2/1993 | European Pat. Off. . | |
| 0532035A3 | 3/1993 | European Pat. Off. . | |
| 2585217 | 1/1987 | France . | |
| 2586558 | 3/1987 | France . | |
| 2677541 | 12/1992 | France . | |
| 2680316 | 2/1993 | France . | |
| 4118359 | 8/1966 | Japan | 604/385.1 |
| 63-123607 | 8/1988 | Japan . | |
| 3-7815 | 1/1991 | Japan . | |
| 4-61523 | 5/1992 | Japan . | |
| 2042342 | 5/1983 | United Kingdom . | |
| 2159693 | 12/1985 | United Kingdom . | |
| 2244422 | 12/1991 | United Kingdom . | |
| 2268073 | 1/1994 | United Kingdom . | |
| WO94/09736 | 5/1994 | WIPO . | |

*Primary Examiner*—John G. Weiss
*Assistant Examiner*—Bruce E. Snow
*Attorney, Agent, or Firm*—Paul Yee

[57] ABSTRACT

A distinctive absorbent article has a front waistband portion, a back waistband portion and an intermediate portion which interconnects the front and back waistband portions. The article comprises a backsheet layer, and an absorbent retention portion superposed on the backsheet layer. A liquid permeable topsheet layer is superposed on the retention portion and connected to sandwich the retention portion between the topsheet and backsheet layers. A laterally extending bridge flap is configured to extend over a body-facing surface of at least one waistband portion of the article. The bridge flap has an elasticized, laterally extending, substantially fixed edge region attached to the at least one waistband portion of the article; an elasticized, laterally extending movable edge region positioned longitudinally inboard of the substantially fixed edge region; and longitudinally extending, substantially fixed side edge regions at laterally opposed side ends thereof. The bridge flap includes a selected width dimension which extends laterally between the bridge flap side edge region and a selected length dimension which extends longitudinally between the fixed and movable edge regions of the bridge flap. The bridge flap movable edge has a substantial extensibility, and has a selected elastic tension. The bridge flap movable edge is desirably arranged to bridge a substantial distance.

19 Claims, 8 Drawing Sheets

U.S. PATENT DOCUMENTS

| | | | |
|---|---|---|---|
| 3,322,122 | 5/1967 | Daniel | 128/284 |
| 3,386,442 | 6/1968 | Sabee | 128/287 |
| 3,400,718 | 9/1968 | Saijo | 128/291 |
| 3,402,715 | 9/1968 | Liloia et al. | 128/287 |
| 3,520,303 | 7/1970 | Endres | 128/287 |
| 3,800,796 | 4/1974 | Jacob | 128/284 |
| 3,881,488 | 5/1975 | Delanty et al. | 128/287 |
| 3,900,031 | 8/1975 | Endres et al. | 128/287 |
| 3,901,236 | 8/1975 | Assarsson et al. | 128/284 |
| 3,930,501 | 1/1976 | Schaar | 128/287 |
| 4,076,663 | 2/1978 | Masuda et al. | 260/17.4 GC |
| 4,286,082 | 8/1981 | Tsubakimoto et al. | 526/240 |
| 4,578,071 | 3/1986 | Buell | 604/379 |
| 4,585,448 | 4/1986 | Enloe | 604/378 |
| 4,627,847 | 12/1986 | Puletti et al. | 604/366 |
| 4,663,220 | 5/1987 | Wisneski et al. | 428/221 |
| 4,699,622 | 10/1987 | Toussant et al. | 604/389 |
| 4,699,823 | 10/1987 | Kellenberger et al. | 428/219 |
| 4,701,170 | 10/1987 | Wilson et al. | 604/385 A |
| 4,704,116 | 11/1987 | Enloe | 604/385 A |
| 4,718,898 | 1/1988 | Puletti et al. | 604/366 |
| 4,738,677 | 4/1988 | Foreman | 604/385 R |
| 4,743,246 | 5/1988 | Lawson | 604/385 A |
| 4,753,646 | 6/1988 | Enloe | 604/385 R |
| 4,778,458 | 10/1988 | Gronostajski | 604/366 |
| 4,795,510 | 1/1989 | Wittrock et al. | 156/64 |
| 4,816,025 | 3/1989 | Foreman | 604/385.2 |
| 4,861,652 | 8/1989 | Lippert et al. | 428/284 |
| 4,938,755 | 7/1990 | Foreman | 604/385.2 |
| 4,981,480 | 1/1991 | Gaudet et al. | 604/386 |
| 4,988,346 | 1/1991 | Pfefferkorn | 604/389 |
| 4,995,873 | 2/1991 | Knight | 604/391 |
| 5,019,066 | 5/1991 | Freeland et al. | 604/385.2 |
| 5,019,073 | 5/1991 | Roessler et al. | 604/391 |
| 5,026,364 | 6/1991 | Robertson | 604/385.1 |
| 5,028,224 | 7/1991 | Pieper et al. | 425/80.1 |
| 5,069,678 | 12/1991 | Yamamoto et al. | 604/385.1 |
| 5,147,343 | 9/1992 | Kellenberger | 604/368 |
| 5,147,347 | 9/1992 | Huang et al. | 604/390 |
| 5,176,670 | 1/1993 | Roessler et al. | 604/391 |
| 5,192,606 | 3/1993 | Proxmire et al. | 428/284 |
| 5,226,992 | 7/1993 | Morman | 156/62.4 |
| 5,269,776 | 12/1993 | Lancaster et al. | 604/387 |
| 5,383,871 | 1/1995 | Carlin et al. | 604/385.2 |

ABSORBENT ARTICLE WITH BRIDGE FLAP

TECHNICAL FIELD

The present invention relates to absorbent articles configured to absorb and retain liquids. More particularly, the present invention relates to absorbent articles having an improved resistance to leakage past the waistband portions of the article.

BACKGROUND OF THE INVENTION

Absorbent articles, such as disposable diapers, have employed various types of absorbent structures to absorb and hold body wastes, such as urine. Typical absorbent articles have included absorbent pads composed of cellulosic fluff and superabsorbent polymer materials.

In an effort to reduce leakage, selected sections of the absorbent articles have incorporated elastic members to provide elasticized sealing and gasketing. For example, leg elastics have been employed to reduce leakage past the leg opening portions of the absorbent articles. In addition, waist elastic members have been employed to reduce leakage past the waistband edges of the articles. In other configurations, liquid impermeable or moisture repellent barriers have been placed along selected edge regions of the absorbent pads. Further configurations of the absorbent articles have incorporated internal, elasticized containment flaps to provide pockets which restrict the sideways movement of waste liquids. For example, see U.S. Pat. No. 4,704,116 issued Nov. 3, 1987, to K. Enloe. Internal, elasticized waist flaps have also been employed to restrict the movement of waste liquids past the waistband edges of the article. For example, see U.S. Pat. No. 4,753,646 issued Jun. 28, 1988, to K. Enloe. Particular absorbent articles have included elasticized barrier flaps in combination with waist flaps composed of an elastic film laminate. The structures have been arranged to restrict movement of liquids along the inner surfaces of the absorbent structure. For example, see U.S. Pat. No. 5,026,364 issued Jun. 25, 1991, to A. Robertson.

Conventional absorbent articles, such as those described above, have not provided desired levels of leakage protection. In particular, undesired gapping between the absorbent article and the body of the wearer along the waistband edges of the article can still allow excessive leakage. For example, when a diaper is placed onto a child, the diaper is typically applied in a manner which fits relatively snugly around the waist and legs, and is typically fastened while the child is lying on his or her back. There can, however, be a 2 inch difference or more between the waist circumference when the child is lying down and when the child is standing or in a sitting position. In addition, the circumference of the child's waist can also change during the course of the child's movements. As a result, there has been a continued need for improved structures which can provide a more effective, liquid-resistent seal along the inner waistband region of the diaper, and a need to further reduce the leakage of liquids past the waistband edges of the absorbent article.

BRIEF DESCRIPTION OF THE INVENTION

Generally stated, the present invention provides a distinctive absorbent article having a front waistband portion, a back waistband portion, and an intermediate portion which interconnects the front and back waistband portions. The article comprises a backsheet layer, and an absorbent retention portion superposed on the backsheet layer. A liquid permeable topsheet layer is superposed on the retention portion and connected to sandwich the retention portion between the topsheet and backsheet layers. A laterally extending bridge flap is configured to extend over a body-facing surface of at least one waistband portion of the article. The bridge flap has an elasticized, laterally extending, substantially fixed edge region attached to the at least one waistband portion of the article, an elasticized, laterally extending movable edge region positioned longitudinally inboard of the substantially fixed edge region, and longitudinally extending, substantially fixed side edge regions at laterally opposed side ends thereof. The bridge flap also has a selected width dimension which extends laterally between the bridge flap side edge regions, and has a selected length dimension which extends longitudinally between the fixed and movable bridge flap edge regions. The bridge flap movable edge region is configured with a predetermined amount of elasticized retractability, as determined with respect to its ungathered width, and is configured with a predetermined level of elastic tension, as determined when the movable edge region is extended to a flat out configuration of the bridge flap.

Another aspect of the invention provides an absorbent article wherein a laterally extending, elasticized bridge flap is connected to extend over an appointed body-facing surface of the article. The bridge flap has a longitudinally extending length dimension thereof, and is constructed to extend laterally beyond opposed side edge regions of at least one waistband portion of the backsheet layer. The bridge flap has a laterally extending, substantially fixed edge region attached to the at least one waistband portion of the article, and a laterally extending movable edge region positioned longitudinally inboard of the substantially fixed edge region.

A further aspect of the invention provides an absorbent article having at least one elasticized side panel connected to a lateral end region of the back waistband portion of the article. The side panel is constructed for interconnecting with the article about a wearer's body to thereby form an assembled bridge flap which is arranged to provide a bodyside surface for contacting the wearer's body. The article includes fastening means for securing the article front waistband portion to the article back waistband portion to thereby encircle the wearer with the waistband portions. The article also includes a waistband-edge attaching means for securing a waistband edge of the assembled bridge flap to the front waistband portion of the article. In particular configurations, the absorbent article can have a pair of elasticized side panels connected at laterally opposed end regions of the back waistband portion of the article, and each of the side panels can include a portion of the waistband-edge attaching means.

In yet another aspect of the invention, the at least one elasticized side panel can optionally include a foldable section which extends length-wise past a longitudinally terminal edge of the backsheet layer. Fold attaching means hold the foldable sections of the side panels in a substantially C-folded condition which wraps about a laterally extending, terminal edge of the article front waistband portion. In particular configurations, the absorbent article can have a pair of elasticized side panels connected at laterally opposed end regions of the back waistband portion of the article. Each of the side panels can include a foldable section which extends length-wise past a longitudinally terminal edge of the backsheet layer. The side panels may be substantially equal or unequal in size, and are constructed for interconnecting with each other about a wearer's body to thereby form the assembled bridge flap.

The various aspects of the present invention can advantageously improve the fit of the absorbent article by reducing rollover at the waist and reducing sagging. The article can also reduce urine leakage, particularly past the waistband edges of the article. The bridge flaps can be stretched around the wearer's waist to form a substantially complete, inner bridging flap which can extend and contract with the wearer's movements while maintaining a substantially continuous inside, inboard contact with the wearer's skin. The movable edge of the bridge flap can also be spaced away from the topsheet of the article to form a pocket which can more effectively trap free-flowing liquids and allow the liquids to be absorbed through the topsheet and into the absorbent retention portion.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants, bed pads and the like.

Figure 1:
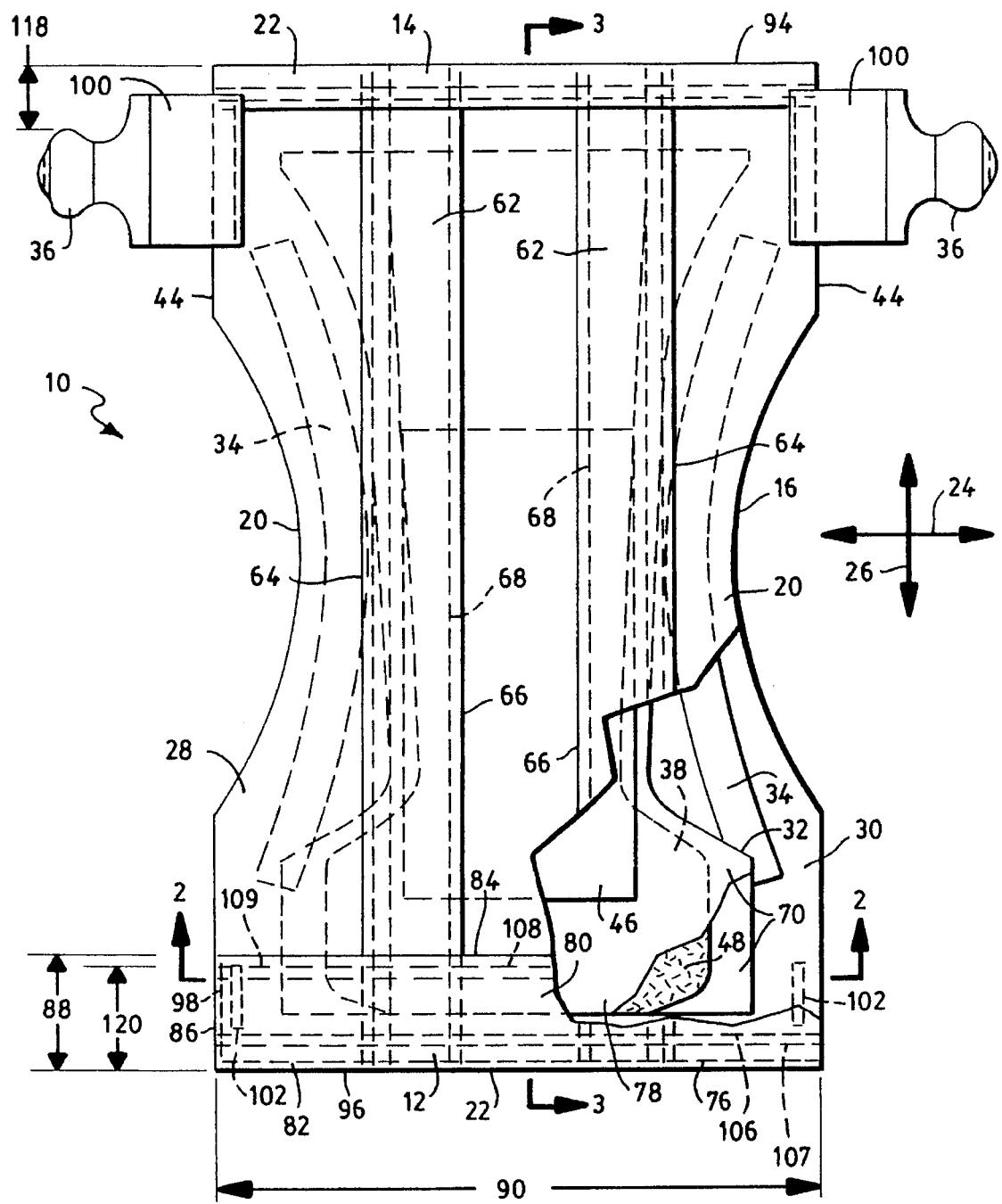
FIG. 1 representatively shows a partially cut-away, top plan view of an article of the invention having an elastically extensible inner waistband structure comprising a bridge flap member.

With reference to FIG. 1, an absorbent article, such as diaper 10, is representatively shown in its extended, flat-out condition with all elastic contractions and gathers removed. The bodyside of the diaper, which is appointed to contact the wearer, is facing the viewer. The outer edges of the diaper define a periphery 18, along which the longitudinally extending side edge margins are designated 20 and the laterally extending end edge margins are designated 22. Preferably, the side edges are curvilinear and contoured to define leg openings for the diaper. The end edges are shown as straight, but optionally, may be curvilinear, as desired. The diaper additionally has a width-wise, laterally transverse dimension 24 and a length-wise, longitudinal dimension 26.

The absorbent article includes a front waistband portion 12, a back waistband portion 14, and an intermediate portion 16 which interconnects the front and back waistband portions. The article includes a backsheet layer 30, and an absorbent body, such as a structure including absorbent retention portion 48, superposed on the backsheet layer 30. A liquid permeable topsheet layer 28 is superposed on the retention portion 48 and connected to sandwich the retention portion between the topsheet and the backsheet layers. A laterally extending bridge flap 80 is configured to extend over a body-facing surface of at least one waistband portion of the article. The bridge flap 80 has an elasticized, laterally extending substantially fixed edge region 82 attached to the at least one waistband portion of the article. The bridge flap also has an elasticized, laterally extending movable edge region 84 positioned longitudinally inboard of the substantially fixed edge region 82, and has longitudinally extending, substantially fixed side edge regions 86 located at laterally opposed side ends of the bridge flap. The bridge flap has a selected width dimension 90 which extends laterally between the bridge flap side edge regions 86, and a selected length dimension 88 which extends longitudinally between the fixed and movable bridge flap edge regions 82 and 84, respectively. In particular configurations, the bridge flap width is at least about 15 cm, and the bridge flap length dimension is at least about 2.5 cm. The bridge flap movable edge region 84 has an elasticized, lateral retractability of at least about 10 percent, as determined with respect to its contracted gathered width, and has an elastic tension within the range of about 40–150 gm-force, as determined when the movable edge region 84 is extended to a flat-out configuration of the bridge flap.

Figure 4:
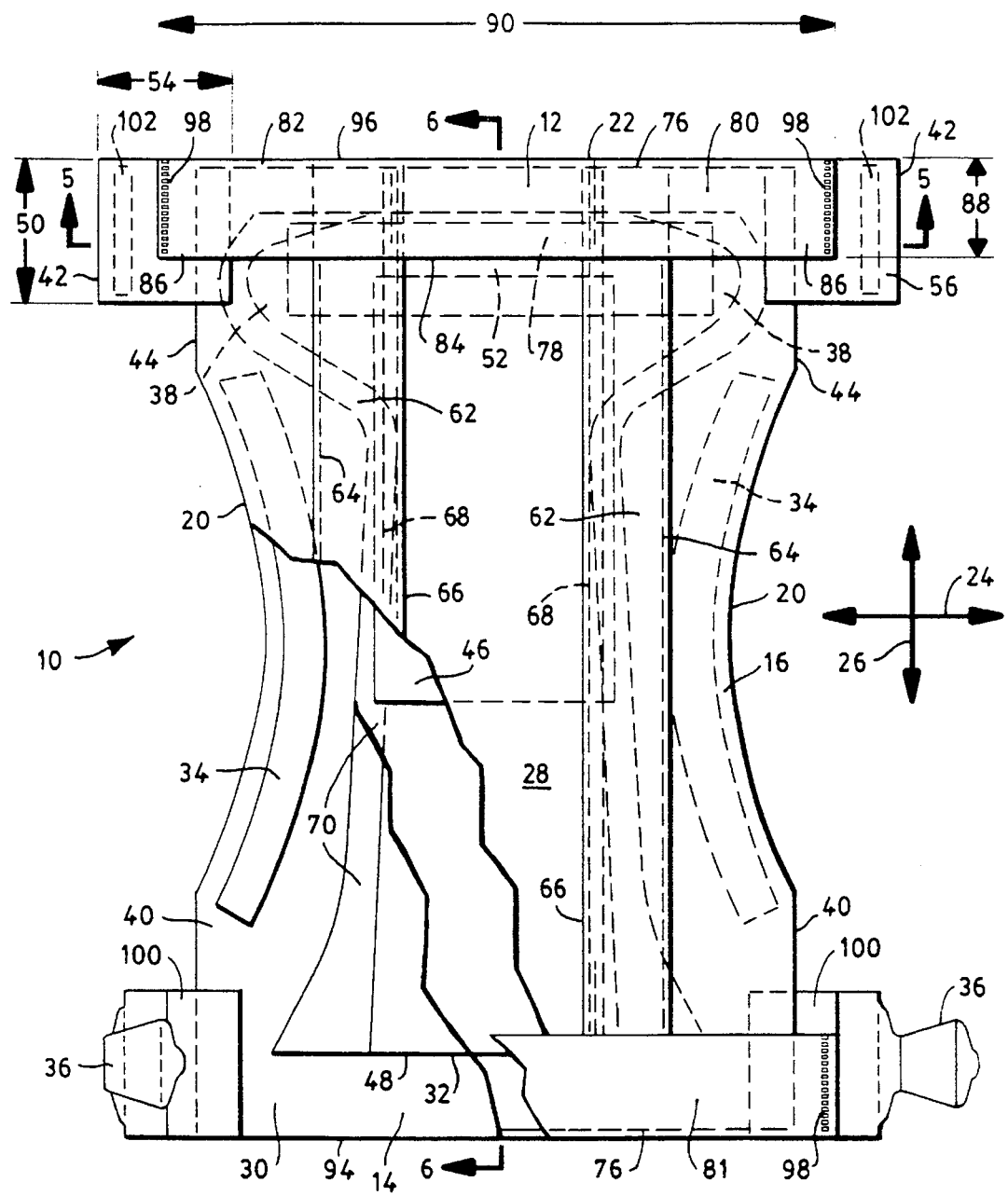
FIG. 4 representatively shows a partially cut-away, top plan view of an absorbent article having a bridge flap connected between a pair of laterally opposed, elastomeric side panels.

With reference to another aspect of the invention illustrated in FIG. 4, an absorbent article, such as diaper 10, has a front waistband portion 12, a back waistband portion 14, and an intermediate portion 16 which interconnects the front and back waistband portion. The article includes a backsheet layer 30, and an absorbent retention portion 48 superposed on the backsheet layer. A liquid permeable topsheet layer 28 is superposed on the retention portion 48 and connected to sandwich the retention portion between the topsheet layer and backsheet layers 28 and 30, respectively. A laterally extending, elasticized bridge flap 80 is connected to extend over an appointed body-facing surface of the article, and is constructed to extend laterally beyond opposed side edge regions, such as edge regions 44, of at least one waistband portion of the backsheet layer 30. In the illustrated example, the bridge flap is associated with the front waistband portion 12 of the article. Alternatively, the bridge flap can be associated with the article back waistband portion 14, or with both the front and back waistband portions 12 and 14 of the article. The bridge flap 80 has a laterally extending, substantially fixed edge region 82 attached to the at least one waistband portion of the article, and a laterally extending movable edge region 84 positioned longitudinally inboard of the substantially fixed edge region 82.

Figure 7:
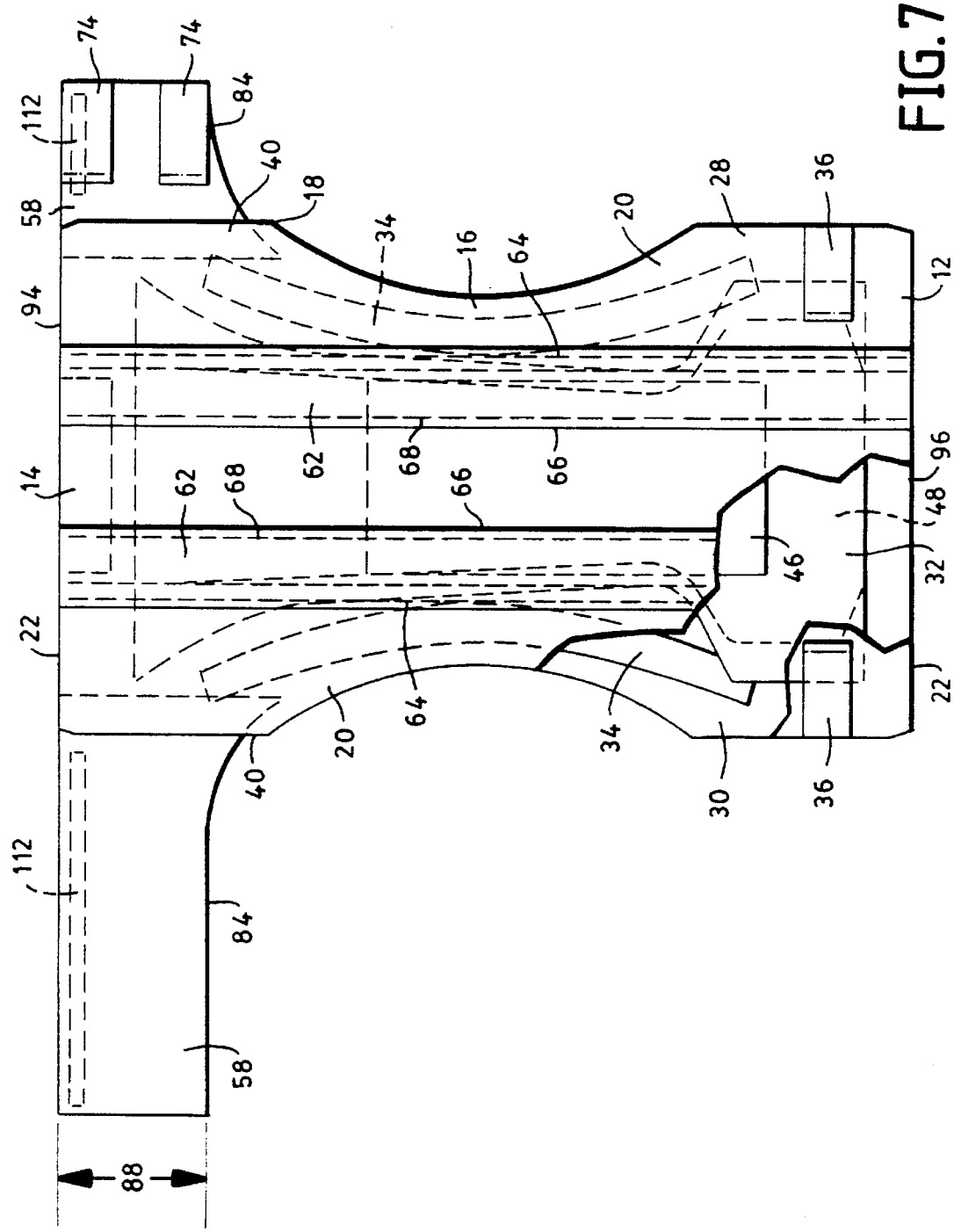
FIG. 7 representatively shows a top plan view of an absorbent article having at least one elastomeric side panel configured with a supplemental waistband-edge attaching means.

With reference to further aspects of the invention illustrated in FIG. 7, an absorbent article has a front waistband portion 12, a back waistband portion 14, and an intermediate portion 16 which interconnects the front and back waistband portions. The article includes a backsheet layer 30, and an absorbent retention portion 48 superposed on the backsheet layer. A liquid permeable topsheet layer 28 is superposed on the retention portion 48 and connected to sandwich the retention portion between the topsheet and backsheet layers. At least one elasticized side panel 58 is connected to at least one end region 40 of the back waistband portion 14 of the article. The side panel 58 is constructed for interconnecting with a cooperating section of the article about a wearer's body to thereby form an assembled bridge flap 180 (e.g. FIG. 8). The assembled bridge flap is arranged to provide a bodyside surface for contacting the wearer. A fastening means, such as flap fasteners 74 can be employed to form the connections that generate the assembled bridge flap. The flap fasteners 74 can be provided by adhesives, cohesives, snaps, hooks, VELCRO® fasteners and the like, as well as combinations thereof. Article fastening means, such as fastener tabs 36, secure the article front waistband portion 12 to the article back waistband portion 14 to thereby encircle the wearer with the article waistband portions. Another attaching means, such as a waistband-edge attaching means 112, secures a laterally extending, longitudinally outboard waistband edge of the assembled bridge flap 180 to a selected section of the front waistband portion of the article. In particular configurations, the absorbent article can include a pair of elasticized side panels 58 connected at laterally opposed end regions of the back waistband portion 14 of the article, and each of the side panels 58 can include an operable portion of the waistband-edge attaching means 112.

Figure 7A:
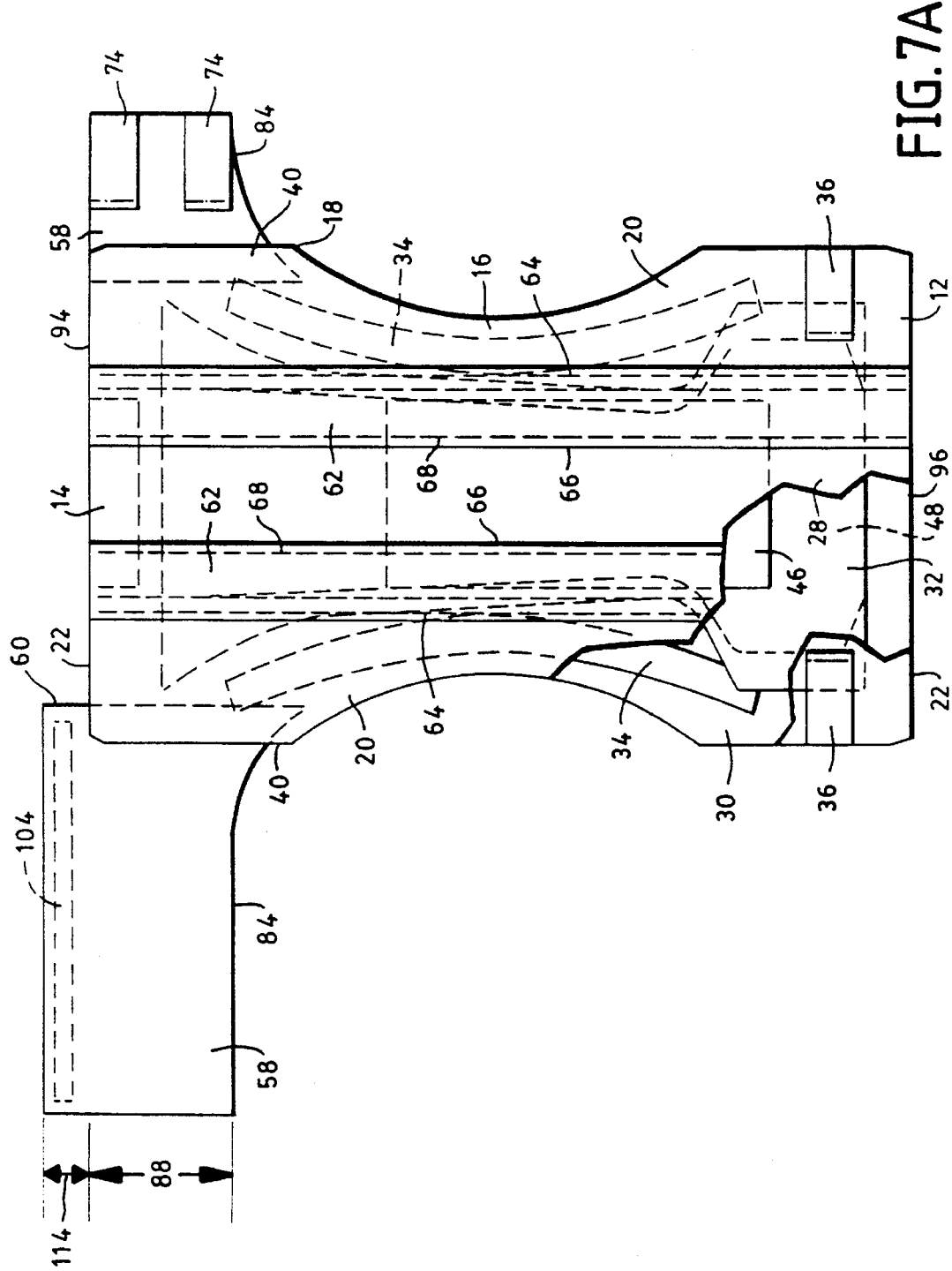
FIG. 7A representatively shows a top plan view of an absorbent article having at least one elastomeric side panel configured with an extending foldable section.
Figure 8:
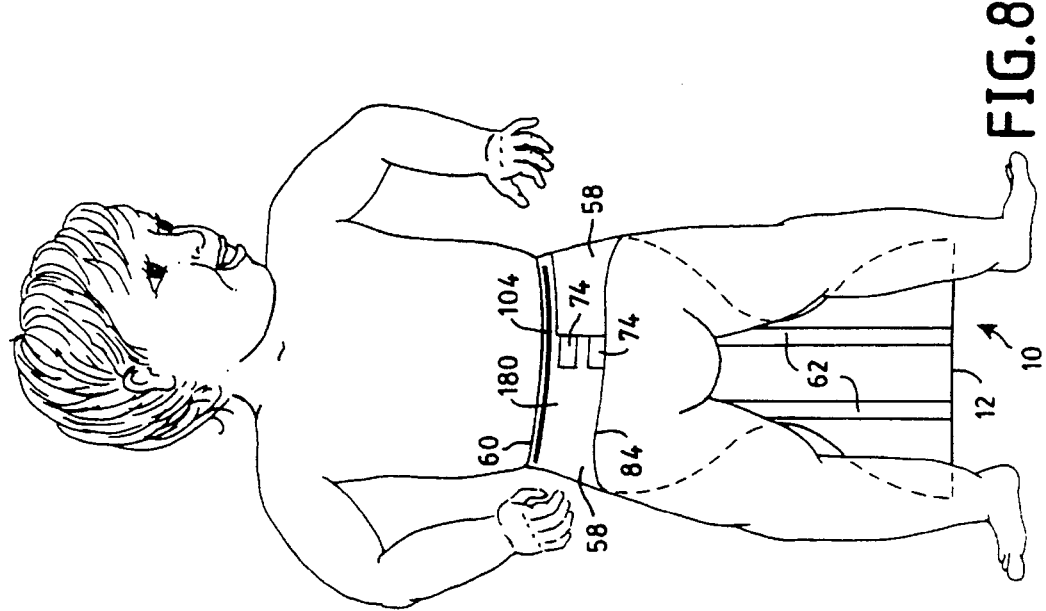
FIG. 8 representatively shows a view of the article of FIG. 7A wherein the elastomeric side panels have been connected about a wearer's body to provide an assembled bridge flap.

As representatively shown in FIG. 7A, the at least one side panel 58 may optionally include a foldable section 60 which extends longitudinally and protrudes length-wise past a longitudinally terminal edge 94 of the backsheet layer 30. The waistband-edge attaching means can be configured to provide a suitable fold attachment means 104. The fold attachments 104 can be constructed to hold the foldable sections 60 of the side panels 58 in a substantially C-folded condition which substantially wraps about a laterally extending, terminal edge 96 of the article front waistband portion 12. Alternatively, a pair of the laterally opposed, elasticized side panels 58 can be connected at laterally opposed end regions 40 of the back waistband portion 14 of the article, and each of the side panels 58 can include a foldable section 60 which extends longitudinally past a longitudinally terminal edge 94 of the backsheet layer 30. The elasticized side panels 58 are constructed for interconnecting with each other about a wearer's body to thereby form the assembled bridge flap 180 (FIG. 8). The assembled bridge flap is arranged to provide a bodyside surface for contacting the wearer, and the flap fastening means, such as provided by flap fasteners 74, can provide the interconnections employed to form the assembled bridge flap. Article fastening means, such as provided by fastener tabs 36, can then secure the article front waistband portion 12 to the article back waistband portion 14 to thereby encircle the wearer with the article waistband portions. An attaching means, such as fold attachments 104, hold the foldable sections 60 of the side panels 58 in a substantially C-folded condition which substantially wraps about a laterally extending, terminal edge 96 of the article front waistband portion 12. The side panels may be unequal in size (FIG. 7) or substantially equal in size, and are constructed for interconnecting with each other about a wearer's body to thereby form the assembled bridge flap.

In the various configurations of the invention, the article represented by diaper 10 can include a liquid permeable topsheet 28; a substantially liquid impermeable backsheet 30; an absorbent body, such as an absorbent structure 32, positioned and operably connected between the topsheet and backsheet; a surge management layer 46 positioned adjacent a major facing surface of topsheet 28; fastener tabs 36; and leg elastic members 34. The various components of the article may be assembled in a variety of well-known configurations. In addition, the various components of the article may be operably interconnected and attached employing conventional securing mechanisms, such as adhesive bonds, sonic bonds, thermal bonds or any other securing means known in the art. For example, a uniform continuous layer of adhesive, a patterned layer of adhesive, a sprayed pattern of adhesive or an array of separate lines, swirls or spots of construction adhesive may be employed.

Absorbent article structures suitable for use with the present invention are described in U.S. Pat. No. application Ser. No. 07/757,778 of D. Proxmire et al., filed Sep. 11, 1991, and entitled ABSORBENT ARTICLE HAVING A LINER WHICH EXHIBITS IMPROVED SOFTNESS AND DRYNESS, AND PROVIDES FOR RAPID UPTAKE OF LIQUID (Attorney Docket No. 9932), now U.S. Pat. No. 5,192,606 issued Mar. 9, 1993, the disclosure of which is hereby incorporated by reference in a manner that is consistent (not contradictory) with the present specification. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. (Attorney Docket No. 9922), the disclosure of which is hereby incorporated by reference in a manner that is consistent herewith.

Figure 2:
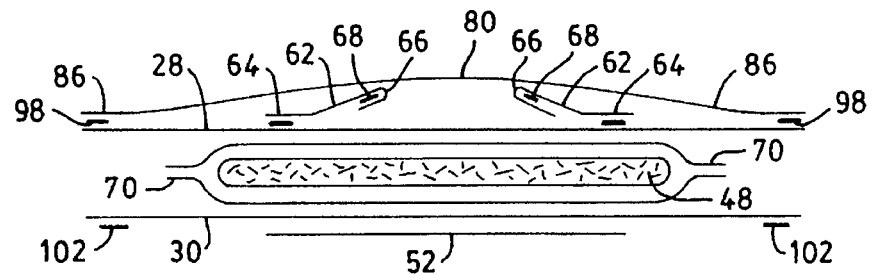
FIG. 2 repesentatively shows a schematic, cross-sectional view taken along a lateral section 2—2 of the article illustrated in FIG. 1.
Figure 3:
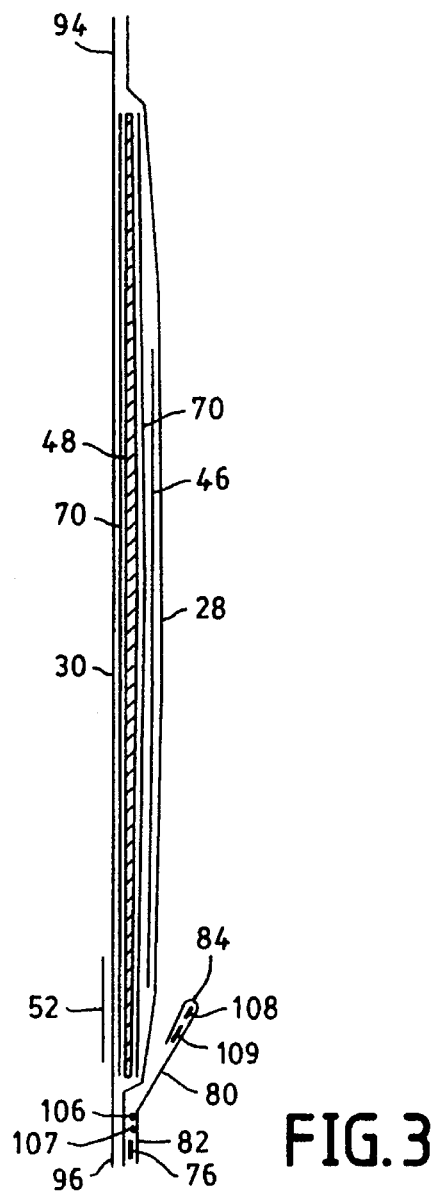
FIG. 3 representatively shows a schematic, expanded, cross-sectional view taken along a length-wise section 3—3 of the article illustrated in FIG. 1.

With reference to the embodiment of diaper 10 representatively shown in FIGS. 1, 2 and 3, topsheet 28 and backsheet 30 can be generally coextensive and can have length and width dimensions which are generally larger than the corresponding dimensions of absorbent structure 32. Topsheet 28 is associated with and superimposed on backsheet 30, thereby defining the periphery 18 of diaper 10, which delimits the outer perimeter or the edges of the diaper 10. The diaper 10 has front and back waistband regions 12 and 14, respectively extending from the laterally extending end edges 22 of diaper periphery 18 toward the transverse center line of the diaper along a distance of from about 2 percent to about 10 percent and preferably about 5 percent of the length of diaper 10. The waistband regions comprise those upper portions of diaper 10, which when worn, wholly or partially cover or encircle the waist or mid-lower torso of the wearer. In particular aspects of the invention, backsheet 30 provides front and/or rear waistbands 12, 14 which are substantially impermeable to liquid. In other aspects of the invention, backsheet 30 may provide front and/or rear waistbands 12, 14 which are substantially impermeable to both liquid and air.

The intermediate, crotch region 16 lies between and interconnects waistband regions 12 and 14. The crotch region comprises that portion of diaper 10 which, when worn, is positioned between the legs of the wearer and covers the lower torso of the wearer. Thus, the crotch region 16 is an area where repeated fluid surges typically occur in diaper 10 or other absorbent article.

Topsheet 28 presents a body-facing surface which is compliant, soft-feeling, and non-irritating when contacting the wearer's skin. Further, topsheet 28 can be less hydrophilic than retention portion 48, and is sufficiently porous to be liquid permeable, permitting liquid to readily penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32.

Various woven and nonwoven fabrics can be used for topsheet 28. For example, the topsheet may be composed of a meltblown or spunbonded web of polyolefin fibers. The topsheet may also be a bonded-carded-web composed of natural and synthetic fibers.

For the purposes of the present description, the term "nonwoven web" refers to a web of material which is formed without the aid of a textile weaving or knitting process. The term "fabrics" refers to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 20 gsm and density of about 0.06 gm/cc. The fabric is surface treated with about 0.28% Triton X-102 surfactant.

In the illustrated embodiment, two containment flaps 62 are connected to the bodyside surface of topsheet layer 28, and extend longitudinally along the article in a generally parallel configuration. Details regarding suitable constructions and arrangements for containment flaps 62 are described, for example, in U.S. Pat. No. 4,704,116 issued Nov. 3, 1987, to K. Enloe, the disclosure of which is hereby incorporated by reference in a manner that is consistent herewith. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (Attorney docket No. 11,375), the disclosure of which is hereby incorporated by reference in a manner that is consistent herewith.

Containment flaps 62, in the shown arrangements, are attached to topsheet layer 28 along fixed edges 64 of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. The containment flaps may be constructed of a material which is the same as or different than the material comprising topsheet 28. In optional embodiments, the containment flaps may be constructed of a material which is the same as or different than the material comprising surge management portion 46. The containment flaps may be composed of a material which is air permeable, liquid permeable, substantially liquid impermeable or combinations thereof.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. The backsheet may be a unitary layer of material or may be a composite layer composed of multiple components assembled side-by-side or laminated.

The various embodiments of backsheet 30 can include protruding ear sections which extend laterally at the waistband portions 12 and 14 of the diaper. The ear sections cooperate with the crotch section of backsheet 30 to operably provide leg opening regions for positioning about the legs of the wearer.

In particular embodiments of the invention, backsheet 30 is a polyethylene film having a thickness of from about 0.012 millimeters to about 0.051 millimeters. In the shown embodiment, the backsheet is a film having a thickness of about 0.032 millimeters. Alternative constructions of the backsheet may comprise a woven or nonwoven fibrous web layer which has been totally or partially constructed or treated to impart the desired levels of liquid impermeability to selected regions that are adjacent or proximate the absorbent body.

In a particular aspect of the invention, a terminal edge of the substantially liquid impermeable backsheet material extends to a position which is substantially coterminous with a front or rear waistband edge of the backsheet member. In the illustrated embodiment, for example, a polymer film comprising backsheet 30 extends to a position which is substantially coterminous with a front or rear waistband edge of the backsheet. Backsheet 30 typically provides the outer cover of the article. Optionally, the article backsheet may comprise one or more separate layers which are in addition to the outer cover layer and may be interposed between the outer cover layer and the absorbent structure.

Backsheet 30 may optionally be composed of a microporous, "breathable" material which permits water vapor to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XK0-8044 polyolefin film available from 3M Company of Minneapolis, Minnesota. The backsheet can also be embossed or otherwise be provided with a matte finish to exhibit a more aesthetically pleasing appearance.

The size and shape of backsheet 30 is typically determined by the size of absorbent structure 32 and the exact diaper design selected. Diaper 10 may, for example, have a generally T-shape, a generally I-shape or a modified hourglass shape, and can define front and/or rear ear portions 38. The backsheet may extend beyond the terminal edges of absorbent structure 32 by a selected distance. Topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

Fastening means, such as tape tab fasteners 36, are typically applied at the lateral, side ends of the back waistband region 14 of diaper 10 to provide a mechanism for holding the diaper on the wearer in a conventional manner. Tape tab fasteners 36 can be any of those well known in the art, and are typically applied to the corners of diaper 10. For example, the article fasteners 36 can be provided by adhesives, cohesives, snaps, hooks, VELCRO® fasteners and the like, as well as combinations thereof. Suitable adhesive tape fasteners are described in U.S. Pat. No. 5,147,347 issued Sep. 15, 1992 to Y. Huang et al. (Attorney Docket No. 9871), the disclosure of which is hereby incorporated by reference in a manner that is consistent herewith. Other suitable fastening systems are described in U.S. patent application Ser. No. 168,615 of T. Roessler et al., entitled DYNAMIC FITTING DIAPER and filed Dec. 16, 1993 (Attorney docket No. 10,961), the disclosure of which is hereby incorporated herein by reference in a manner that is consistent herewith.

Elastic members 34 are disposed adjacent periphery 18 of diaper 10. Along each side edge region 20, leg elastic members 34 are arranged to draw and hold diaper 10 against the legs of the wearer. Waist elastic members may optionally be disposed adjacent either or both of the end edges 22 of diaper 10 to provide elasticized waistbands.

The various elastic members are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several separate, parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive. The various configurations of the invention may have the elastic members located on the inwardmost, bodyside surface of topsheet 28. Alternatively, the elastic members may be interposed between topsheet 28 and backsheet 30.

In the representatively shown embodiments of the invention, the illustrated leg elastic members 34 may comprise a carrier sheet 37 to which are attached a grouped set of elastics composed of a plurality of individual elastic strands 39. The elastic strands may intersect or be interconnected, or be entirely separated from each other. The shown carrier sheet may, for example, comprise a 0.002 cm thick film of unembossed polypropylene material. The shown elastic strands can, for example, be composed of Lycra® elastomer available from DuPont, a business having offices in Wilmington, Del. Each elastic strand is typically within the range of about 620–1050 decitex (dtx), and can be about 940 dtx in an embodiment of the invention wherein three strands are employed for each elasticized legband.

Leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 1.9–3.8 centimeters (about 0.75–1.5 inches) inward from the outer most edge of the set of elastic strands. In particular arrangements, the curvature of the elastics may not be configured or positioned symmetrically relative to the lateral centerline of the diaper. As representatively shown in FIG. 1, the curved elastics may have an inwardly bowed and outwardly bowed, reflexed-type of curvature, and the lengthwise center of the elastics may be offset by a selected distance within the range of about 0–12 cm toward either the front or rear waistband of the diaper to provide desired fit and appearance.

The elastic members can be composed of an elastomeric, cloth-like nonwoven fibrous material, such as an elastomeric stretch-bonded laminate (SBL) web or an elastomeric meltblown web. Examples of suitable meltblown elastomeric fibrous webs for forming the elastic members are described in U.S. Pat. No. 4,663,220 issued May 5, 1987, to T. Wisneski, et al., the disclosure of which is hereby incorporated by reference in a manner that is consistent with the present description. Examples of composite fabrics comprising at least one layer of nonwoven textile fabric secured to a fibrous elastic layer are described in European Patent Application EPA 0 110 010 published Apr. 8, 1987, with the inventors listed as J. Taylor et al. now E0 0217032, the disclosure of which is hereby incorporated by reference in a manner that is consistent herewith. The composite nonwoven fabrics are commonly referred to as stretch-bonded laminates.

In yet another aspect of the invention, the elastic members can be composed of an elastomeric, stretchable composite web comprising individual, discrete strips of elastomeric material secured to one or more nonwoven fibrous layers. Such a composite web may, for example, comprise an elastomeric meltblown material arranged in a selected pattern of strips and suitably sandwiched and attached between two layers of nonwoven, spunbonded fibrous material. The composite web may alternatively comprise a selected pattern of individual elastomeric strips operably secured to a nonwoven fibrous layer or between two nonwoven layers. The elastomer strips may, for example, be composed of a thermoplastic, melt extrudable material. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylenepropylene diene monomer) rubbers, EPM (ethylene-propylene monomer) rubbers, blends of EPDM/EPM/EVA, and the like.

An absorbent body, such as provided by absorbent structure 32, is positioned between topsheet 28 and backsheet 30 to form diaper 10. The absorbent body has a construction which is generally compressible, conformable, non-irritating to the wearer's skin. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Alternatively, each piece is connected to an adjacent portion of the absorbent structure by a suitable bonding and/or fiber entanglement mechanism, such as ultrasonic or adhesive bonding, or mechanical or hydraulic needling.

Absorbent structure 32 includes a back section and a front section, and provides a liquid acquisition, target zone. The target zone encompasses the area where repeated liquid surges typically occur in absorbent structure 32. The particular location where liquid is discharged, such as during urination, can vary depending on the age and gender of the wearer. Generally stated, the target zone is a section of absorbent structure 32 which is located in the front 60% of the length of the absorbent structure.

Either or both of the back and front sections can include laterally extending ear regions 38 which provide greater width at the waistband sections of the article. When the diaper is worn, the ear regions are configured to extend about the sides of the wearer's waist and torso. The representatively shown absorbent structure has a contoured, curvilinear periphery, particularly along its side edges. The two generally mirror-image, inwardly bowed, lateral edges provide for a narrower intermediate section suitable for positioning in the crotch of the wearer.

With respect to absorbent articles, wherein reduced bulk or reduced cost may be important, the surge management and retention portions need not extend over the entire, overall shape of the garment. In particular configurations of the invention, for example, retention portion 48 can be asymmetrically located along the length of backsheet 30, with at least about 45 percent of the length of the retention portion located in a front half-section of backsheet 30. Alternatively, at least about 55 percent of the retention portion length is located in the front half-section of backsheet 30, and optionally, at least about 65 percent of the retention portion length is located in the front half-section of the backsheet to provide desired attributes. Similar asymmetric positionings of the surge management portion 46 may also be employed.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In the shown arrangements of the invention, for example, absorbent structure 32 can be generally T-shaped with the laterally extending cross-bar of the "T" generally corresponding to the front waistband portion of the absorbent article for improved performance, especially for male infants. In the illustrated embodiments, the absorbent structure across the ear section of the front waistband region of the article has a cross-directional width of about 9 inches (about 23 cm), the narrowest portion of the crotch section has a width of about 3.5 inches (about 8.9 cm) and the back waistband region has a width of about 4.5 inches (about 11.4 cm).

In a particular aspect of the invention, the absorbent structure has an absorbent capacity of at least about 100 gm of saline. Optionally, the absorbent capacity can be at least about 200 gm of saline. Alternatively, the absorbent structure has an absorbent capacity of at least about 300 gm of saline, and optionally has an absorbent capacity of at least about 400 gm of saline to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

For the purposes of the present invention, the term "hydrophilic" refers to fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for components of the invention can be provided by a Cahn SFA-222 Surface Force Analyzer System. When measured with this system, fibers having contact angles less than 90° are designated "wettable", while fibers having contact angles greater than 90° are designated "nonwettable".

In the various configurations of absorbent structure 32, the retention portion 48, with respect to its total weight, can contain at least about 25 weight percent (wt %) of high absorbency material. Alternatively, the retention portion can contain at least about 50 wt % of high absorbency material, and optionally can contain at least about 75 wt % of high absorbency material to provide desired benefits. The high-absorbency material employed with the various aspects of the invention may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48. Desireable for use are particles having an average size of from about 20 micrometers to about 1 millimeter.

Selected superabsorbent polymers having improved absorbent properties can be important for maximizing the performance while retaining the desired thinness of the absorbent article. For example, in arrangements of the invention having high-absorbency material mixed with hydrophilic fibers, the high-absorbency material can be configured to exhibit a Deformation Under Load which is about 0.6 millimeter or less. In other aspects of the invention, the high-absorbency material can exhibit a Wicking Index which is about 10 centimeters or greater, and the Absorbent Capacity of the high-absorbency material is about 28 grams per gram or greater. In further aspects of the invention, the high-absorbency material can exhibit a Wicking Parameter which is about 700 or greater, preferably is about 800 or greater, more preferably is about 850 or greater, and most preferably is about 900 or greater. In still other aspects of the invention, the high-absorbency material can exhibit an Absorbency Under Load (measured at a pressure of 0.57 psi) which is about 13 or greater. An example of a suitable superabsorbent polymer is SANWET IM3900 polymer, which is available Hoechst Celanese, a business having offices in Portsmouth, Va. Details regarding the determination of the Deformation Under Load, Wicking Index, Absorbent Capacity, Wicking Parameter and Absorbency Under Load are set forth in U.S. patent application Ser. No. 906,001 of S. Byerly et al. filed Jun. 26, 1992 and entitled ABSORBENT COMPOSITES AND ABSORBENT ARTICLES CONTAINING SAME (Attorney docket No. 10174.1), the disclosure of which is hereby incorporated by reference in a manner that is consistent herewith.

It has been discovered that the performance of a superabsorbent material relates to the ability of the superabsorbent material to absorb a liquid not only while under a single given restraining force, such as about 0.3 pound per square inch (about 2 kPa), but also over a broader range of restraining forces, such as about 0.01–0.9 pound per square inch (about 0.7–6.2 kPa). The ability of a superabsorbent material to absorb a liquid under a variety of different restraining pressures has, for the purposes of this application, been quantified as the Pressure Absorbency Index. Superabsorbent materials useful in the present invention may also suitably have a 16-hour extractables level of less than about 13 weight percent. A particular example of a high absorbency material suitable for use in the present invention is FAVOR SAB 870 superabsorbent polymer produced by Stockhausen, Inc., a business having offices in Greensboro, N.C.

Suitable techniques for determining desired parameters, such as a desired AUL value, Pressure Absorbency Index and extractables level of the high absorbency material are set forth in copending U.S. patent application Ser. No. 016,312; entitled ABSORBENT COMPOSITE; of M. Melius et al.; filed on Feb. 24, 1993 (Attorney Docket No. 10,838); and in its associated continuation-in-part application filed on Oct. 29, 1993; the disclosures of which are hereby incorporated by reference in a manner that is consistent herewith.

The representatively shown examples of a retention portion 48 can comprise a matrix of hydrophilic fibers, such as a web of cellulosic woodpulp fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the retention portion, with lower concentrations toward the bodyside of the retention portion and relatively higher concentrations toward the outerside of the retention portion. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers. In addition, two or more different types of superabsorbent may be selectively positioned at different locations within or along the fiber matrix.

The invention can, for example, be configured to provide a medium-size article which has been referred to as a "STEP 3" size diaper. Such articles can comprise a retention portion 48 in the form of a fluff pad which includes 4–25 grams of woodpulp fluff. The pad can alternatively include about 5–20 grams of fluff, and can optionally include about 6–15 grams of fluff to provide desired benefits. The woodpulp fluff generally provides shape and form to diaper 10, and carries and positions the particles of superabsorbent polymer or other high-absorbency material. The fluff pad can also contain about 1–16 grams of superabsorbent polymer, and in the shown embodiment, the retention portion can contain 4–12 grams superabsorbent polymer.

The hydrophilic fibers and high-absorbency particles can be configured to form an average composite basis weight which is within the range of about 250–900 gsm. Again, such basis weight is particularly desireable in the target zone of the absorbent structure. In certain aspects of the invention, the average composite basis weight is within the range of about 400–800 gsm, and optionally is within the range of about 450–700 gsm to provide desired performance.

The density of retention portion 48 or other component of the absorbent article can be calculated from its basis weight and thickness. With respect to diapers, for example, the weight and thickness are measured with respect to samples taken from newly unpacked, unfolded and dry diapers at a restraining pressure of 0.2 psi (1.38 kPa). For measuring thickness, a suitable device is a TMI foam thickness gauge, Model No. TM1-49-21 or its equivalent. The apparatus was obtained from Testing Machines, Inc. of Amityville, N.Y.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material can be distributed down a medial region of retention portion 48 which extends along the length dimension of the retention portion. In addition, the superabsorbent material may have a selected zoned placement to reduce the amount of superabsorbent material located proximate both the side and end edges of the retention portion. The reduced amounts of superabsorbent material at the edges of the retention portion can help improve the containment of the superabsorbent particles within the fibrous fluff matrix of retention portion 48. The pulsed, zoned placement of the superabsorbent material can, for example, be achieved by the method and apparatus described in copending U.S. patent application Ser. No. 07/462,363 of C. Pieper et al. filed Jan. 9, 1990, and entitled METHOD AND APPARATUS FOR INTERMITTENTLY DEPOSITING PARTICULATE MATERIAL IN A SUBSTRATE (Attorney Docket No. 8761), the disclosure of which is hereby incorporated by reference in a manner that is consistent herewith.

As representatively shown, the retention portion 48 composed of the absorbent fluff-superabsorbent matrix, can be laminated with or overwrapped in a hydrophilic high wet-strength web provided by one or more face sheets 70. The face sheet can, for example, include a high wet-strength tissue or a synthetic fibrous web. Such an overlying or overwrapping web can increase the in-use integrity of the absorbent structure.

The face sheet structure may comprise a single layer of face sheet material, or may comprise a multi-element sheet which includes a separate bodyside face layer and a separate outerside face layer. In the multi-element configuration, each face layer can extend past all or some of the peripheral edges of retention portion 48. Such a configuration of the face sheet layers can, for example, facilitate the formation of a substantially complete sealing and closure around the peripheral edges of retention portion 48. In the illustrated embodiment, the bodyside and outerside layers of face sheet 70 extend at least about 0.5 inch (about 1.27 cm) beyond the peripheral edges of the retention portion to provide an outwardly protruding, flange-type bonding area over which the periphery of the bodyside face sheet layer may be completely or partially connected to the periphery of the outerside face sheet layer.

The bodyside and outerside layers of a multi-element face sheet 70 may be composed of substantially the same material, or may be composed of different materials. For example, the outerside face sheet may be composed of a relatively lower basis weight material having a relatively high porosity, such as a wet strength cellulosic tissue composed of softwood pulp.

To provide any desired bonding between the individual bodyside and outerside portions of the multi-element face sheet 70, an adhesive can be printed or otherwise applied onto the appointed bonding areas of the face sheet. With reference to the article representatively shown in FIG. 1, for example, a rotogravure-type adhesive applicator may be employed to selectively print a National Starch 33-9156 adhesive composed of a polyvinylacetate-based emulsion. The retention portion 48 can then be placed between the bodyside and outerside portions of face sheet 70, and the mating edges of the face sheet portions can be bonded together to provide a generally complete peripheral seal along substantially the entire perimeter of the retention portion.

In other configurations of the invention, the retention portion 48 can comprise a superabsorbent laminate having superabsorbent particles segregated in separate, discrete pockets regions formed in the laminate structure. The laminate can include at least one, liquid permeable carrier layer which holds and maintains the superabsorbent particles in the pocket regions. Suitable laminate structures are described in U.S. patent application Ser. No. 145,926 entitled ABSORBENT ARTICLE WHICH INCLUDES SUPERABSORBENT MATERIAL LOCATED IN DISCRETE ELONGATED POCKETS PLACED IN SELECTED PATTERNS and filed Oct. 29, 1993 by R. Tanzer et al. (Attorney docket no. 10,902), the disclosure of which is incorporated herein by reference in a manner that is consistent herewith.

Due to the thinness of retention portion 48 and the high superabsorbent concentrations within the retention portion, the liquid uptake rates of the retention portion, by itself, may be too low, or may not be adequately sustained over three insults or doses of liquid into the absorbent structure. The addition of a layer of surge management material into the absorbent structure, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point to selected regions of absorbent structure 32, where the liquid can be substantially completely released into retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web composed of natural and synthetic fibers. The surge management portion may be composed of a substantially hydrophobic material, and the hydrophobic material may optionally be treated with a surfactant or otherwise processed to impart a desired level of wettability and hydrophilicity.

The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0–3.0 inch (about 2.54–7.62 cm).

The absorbent article represented by diaper 10 can include a liquid surge management portion 46 and an absorbent retention portion 48 which is adjacently arranged in a direct, contacting liquid communication with the surge management portion. In the illustrated embodiment, for example, the surge management portion is positioned on the bodyside of retention portion 48. Optionally, the surge management portion may be positioned on the outer side of the retention portion.

The various aspects of the invention can also provide an absorbent article having a surge management portion 46, which may be located on a outerside surface of topsheet 28 which faces toward backsheet 30 (FIG. 1), or alternatively, may be located on an opposite, bodyside surface of the topsheet (not shown). In optional arrangements of the invention, the surge management portion may be cooperatively arranged with a multi-piece topsheet. Such a topsheet configuration can, for example, include two, individual topsheet sections which are laterally spaced-apart from each other along the diaper cross-direction, and an intermediate surge management portion which is operatively connected to bridge therebetween. The surge management portion thereby provides the medial section of the topsheet composite assembly.

In the various embodiments of the invention, at least a part of surge management portion 46 is located within the target zone of the absorbent structure, and in particular arrangements, the surge management portion has an areal extent which extends completely over the target zone. Retention portion 48 is positioned in liquid communication with surge management portion 46 to receive liquids released from the surge management portion and to hold and store the liquid. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The shown arrangement of the surge management portion is substantially free of absorbent gelling material. Surge management portion 46 may, however, contain a very small amount of gelling material to help acquire an initial liquid surge, but the amount should not be excessive. When excessive amounts of absorbent gelling material are maintained in surge management portion 46, however, the gelling material can cause the structure to retain and hold unacceptably high amounts of the liquid. In addition, the transport of liquids away from target zone 53 to other sections of absorbent structure 32, particularly retention portion 48, can be undesirably impaired.

As mentioned previously, surge layer 46 can be a separately formed layer, which lies adjacent the outerwardly facing surface of topsheet 28 between the retention portion and topsheet. Thus, surge management portion 46 need not extend through the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in the generally sideways (X-Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, the surge management portion can be generally rectangular-shaped.

Other suitable configurations the surge management portion 46 are described in U.S. Pat. No. 5,192,606 of D. Proxmire et al. issued Mar. 9, 1993 (Attorney docket No. 9932); U.S. patent application Ser. No. 757,760 of W. Hanson et al. filed Sep. 11, 1991 (Attorney docket No. 9922); U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No.

11,387); the disclosures of which are hereby incorporated by reference in a manner that is consistent herewith.

In the various embodiments of the invention, the surge layer width is within the range of about 16–100% of the topsheet width. The surge layer width is alternatively at least about 24% of the topsheet width, and optionally, is at least 50% of the topsheet width to provide desired levels of effectiveness.

The various embodiments of surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within front section 49 of absorbent structure 32. Thus, surge management portion 46 can be approximately centered about the longitudinal center line of absorbent structure 32, and positioned primarily in central, front section of the absorbent structure 32. In the illustrated embodiment, none of surge management portion 46 is located in the ear regions of the absorbent structure.

With the various embodiments of the invention, the basis weight of surge management portion 46 can be at least about 24 grams per square meter (gsm), alternatively is at least about 40 gsm, and optionally is at least about 45 gsm to help provide the total void volume capacity desired for effective operation. In a particular aspect of the invention, the basis weight is not more than about 300 gsm, alternatively, is not more than about 150 gsm, and optionally, is not more than about 100 gsm to provide desired advantages. It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections.

During the typical use of the article, the front panel and front waistband region 12 of the diaper extend and curve around the front of the wearer's body, and the back panel and back waistband region 14 of the diaper extend and curve around the back of the wearer's body. Fastening means, such as fastener tabs 36, attach the diaper back waistband region 14 to the diaper front waistband region 12 to secure the article on the wearer. The diaper front waistband region forms an arc which is intended to contact the wearer's body. The wearer's stomach region, however, can contract due to breathing or other movements and may, from time to time, lose contact with the diaper front waistband region. It has been found that the front arc of the wearer's stomach may decrease as much as 2.5 inches (6 cm). Even when the article includes elastomerics, such as elasticized waistbands or elasticized side panels, the waistband regions 12 and 14 of the article may not sufficiently contract to maintain substantially continuous contact with the changing circumference of the wearer's body.

To help address the shortcomings of conventional structures, the present invention employs a bridge flap 80 having a distinctive combination of extensibility, retractability, and bridge forming capability. To maintain a substantially continuous, positive contact with the wearer's waist, at least a selected movable portion of the bridge flap 80 is constructed to have a high degree of retractability. In particular configurations of bridge flap 80, the level of retraction can be as much as 6 cm or more. It has been found that the retracted width-wise extent of the bridge flap movable edge 84 should be at least 1 cm shorter than the retracted width of the bridge flap fixed edge 82. In further configurations of the invention, the retracted dimension of bridge flap movable edge 84 is at least about 6 cm shorter than the retracted width of the bridge flap fixed edge 82.

In the various aspects of the invention, the bridge flap member can be composed of a material which provides a soft, hydrophobic, non-irritating surface appointed for placement adjacent a wearer's skin. In particular configurations, the bridge flap material can comprise a fibrous layer which permits a movement of gas therein and substantially avoids excessive occlusion of the wearer's skin. Examples of suitable materials for constructing bridge flap 80 include perforated films, such as perforated polyethylene films; nonwoven fabrics, such as spunbonded webs and bonded-carded-webs composed of synthetic polymer fibers; tissues; meltblown fibrous webs; airformed fibrous webs which have been suitably bonded to provided desired integrity; as well as laminates and other combinations thereof.

The bridge flap material can be permeable to a passage of gas through a thickness dimension thereof. In other arrangements, the bridge flap material can be highly resistant to a passage of liquid through its thickness. In addition, the bridge flap material can be substantially nonwettable to avoid excessive wicking and transport of liquid along its surfaces. In the various configurations of the invention, the bridge flap extends over a flap surface area and is selectively elasticized to provide desired performance. For example, the bridge flap can be elasticized by constructing the flap of an elastic material, such as an elastic laminate, which is stretchable along a lateral cross-direction of the article and operably elasticizes a substantial entirety of the flap surface area. Alternatively, the operable bridge flap can be elasticized by connecting at least one separate elastic member, in an elastically contractible condition, to the bridge flap. The elastic member is stretchable at least along the article cross-direction and operably elasticizes one or more selected strip regions of the flap surface area.

With reference to FIG. 1, the bridge flap 80 has a cross-directional width dimension 90, a longitudinally extending length dimension 88, a substantially fixed edge region 82, and a substantially movable edge region 84. The bridge flap 80 also includes side end regions 86, which may optionally be secured to the article with suitable side edge securement means 98. Where bridge flap 80 has its side end regions 86 secured to the article with side edge securement means 98, the width dimension of bridge flap fixed edge 82 is determined by the lateral distance between the side edge securement at one side edge region 86 to the securement means at the laterally opposed and distally spaced side edge region of the bridge flap.

The embodiment representatively shown in FIGS. 1, 2 and 3, illustrates the configuration of the invention where the bridge flap is elasticized by a selected system of separate and discrete elastic members which are operably connected to selected strip sections of the bridge flap. The elastic members can be attached to either or both of the fixed and movable edge regions 82 and 84, respectively, of the bridge flap 80. In particular, one or more movable edge elastics, such as elastics 108 and/or 109, can be operably connected to movable edge region 84 to provide selected levels of extensibility and elastic tension to the movable edge region of the bridge flap 80. Alternative configurations of the substantially fixed edge region 82 of bridge flap 80 can include at least one fixed edge elastic 106, and optionally can include a plurality of fixed edge elastics 106 and 107 to provide a selected level of extensibility and elastic tension to the fixed edge region 82. The bridge flap elastics at the movable and/or fixed edge regions of the bridge flap 80 can, for example, be provided by strands of Lycra® elastomeric material.

The movable edge elastics 108 and/or 109 extend along at least about 15% of the cross-directional width of the movable edge 84. Alternatively, the movable edge elastics can extend along at least about 50%, and optionally about 80% of the cross-directional width of the movable edge to provide improved performance. In the shown embodiment, the movable edge elastics extend along approximately 100% of the cross-directional width of the movable edge 84. If the movable edge elastics are too short, the bridge flap 80 may not adequately span across gaps occurring along the article waistband.

In particular aspects of the invention, the elasticized, lateral retractability of the bridge flap movable edge region 84 is at least about 10 percent. Alternatively, the elasticized retractability is at least about 25 percent and optionally is at least about 40 percent to provide improved performance.

The retractability of a selected region of the article, such as bridge flap movable edge 84, can be determined by the following formula:

$$\frac{(A-B)}{A} \times 100 \text{ percent;}$$

wherein
- A=the fully extended length of the selected article portion with substantially all elastic contractions in the selected region of the article removed;
- B=the retracted length of the selected article portion where the article portion is substantially untensioned by external forces, and is allowed to freely retract and gather.

In further aspects of the invention, the elasticization of the bridge flap movable edge 84, such as provided by elastics 108 and 109, can provide a total elastic tension of at least about 10 grams force along the movable edge 84. Alternatively, the elastic tension is at least about 15 grams force, and optionally is at least about 20 grams force to provide desired benefits. In addition, the elastic tension provided at the movable edge 84 can be not more than about 250 grams force. Alternatively, the elastic tension is not more than about 200 grams force, and optionally is not more than about 150 grams force to provide improved performance.

If the retractability and elastic tension of bridge flap movable edge section 84 is too small, the bridge flap may have insufficient ability to span across any gaps which may be produced between the article waistband and the wearer's body. If the elastic tensions are too large, the lateral ends of the article waistband portion may be excessively pulled in toward the lateral center of the diaper, and create undesired tucks and folds at the lateral ends of the front waistband portion 12 of the article.

With regard to the embodiment representatively shown in FIG. 1, bridge flap 80 can have a width dimension of at least about 10 cm. Alternatively, the bridge flap member can have a width dimension of at least about 12.5 cm, and optionally can have a width dimension of at least about 15 cm. In other aspects of the invention, bridge flap 80 can have a width dimension 90 which is not more than about 35.5–40.6 cm. More particularly, the width dimension can be not more than about 38 cm. Alternatively, the bridge flap width dimension can be not more than about 36 cm, and optionally can be not more than about 33 cm to provide desired performance. The bridge flap 80 can also have a length dimension 88 which is at least about 0.5 cm. Alternatively, the bridge flap length dimension is at least about 0.8 cm, and optionally is at least about 1 cm. In the representatively shown embodiment, for example, the bridge flap length is not less than about 4 cm. In further aspects of the invention, the bridge flap 80 can have a length dimension which is not more than about 9–12.7 cm. More particularly the length dimension can be not more than about 10 cm. Alternatively, the bridge flap length dimension is not more than about 9 cm, and optionally is not more than about 7.5 cm to provide desired performance.

With regard to an adult incontinence product, bridge flap 80 can have a width dimension of at least about 25.4 cm. Alternatively, the bridge flap member can have a width dimension of at least about 30.5 cm, and optionally can have a width dimension of at least about 35.5 cm. In other aspects of the adult-size product, bridge flap 80 can have a width dimension 90 which is not more than about 89 cm. Alternatively, the bridge flap width dimension can be not more than about 76 cm, and optionally can be not more than about 63.5 cm to provide desired performance. The bridge flap 80 can also have a length dimension 88 which is at least about 2.5 cm.

Alternatively, the bridge flap length dimension is at least about 3.8 cm, and optionally is at least about 5 cm. In further aspects of the adult product, bridge flap 80 has a length dimension which is not more than about 15.5 cm. Alternatively, the bridge flap length dimension is not more than about 12.7 cm, and optionally is not more than about 10.2 cm to provide desired performance.

In the various configurations of the invention, the substantially fixed edge 82 of the bridge flap 80 is operably attached to a body-facing surface of the article, such as the bodyside surfaces of topsheet 28 and containment flaps 62 (FIG. 1), as well as side panels 56 (FIG. 4). The desired attachments between bridge flap 80 and the bodyside surface of the article can be provided by any suitable securing means. For example, the securing means may comprise adhesive bonds, thermal bonds, ultrasonic bonds, or the like, as well as combinations thereof. In addition, the attachments along bridge flap fixed edge 82 and along bridge flap side end regions 86 can be configured to provide a liquid-resistant, substantially liquid-impermeable barrier seal between the fixed edge region of the bridge flap member and the immediately underlying section of the article. In particular configurations, the liquid-resistant barrier can be constructed to extend from barrier flap 80 to backsheet layer 30. Similarly, the bridge flap can include laterally opposed, longitudinally extending side end regions 86. The side edge regions of bridge flap 80 can also include longitudinally extending securement means 98 for operably attaching the bridge flap to selected portions of the article. In particular configurations, the securement means 98 provide liquid-resistant barrier seals between the bridge flap member 80 and the appointed attached sections of the article, such as topsheet 28 or side panel members 56. As a result, the barrier seals can help prevent undesired migration of liquid through the topsheet layer material at the longitudinally outboard waistband edge or the laterally outboard edges of the bridge flap.

Figure 5:
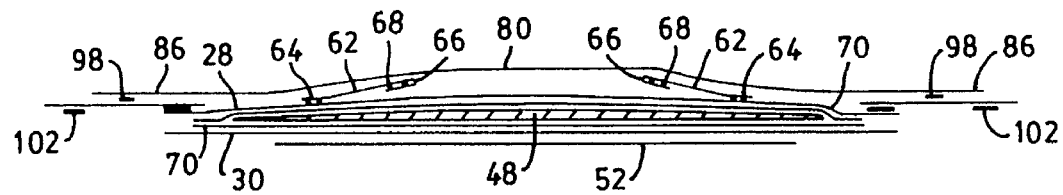
FIG. 5 representatively shows a schematic, cross-sectional view taken along a lateral section 5—5 of the article illustrated in FIG. 4.
Figure 6:
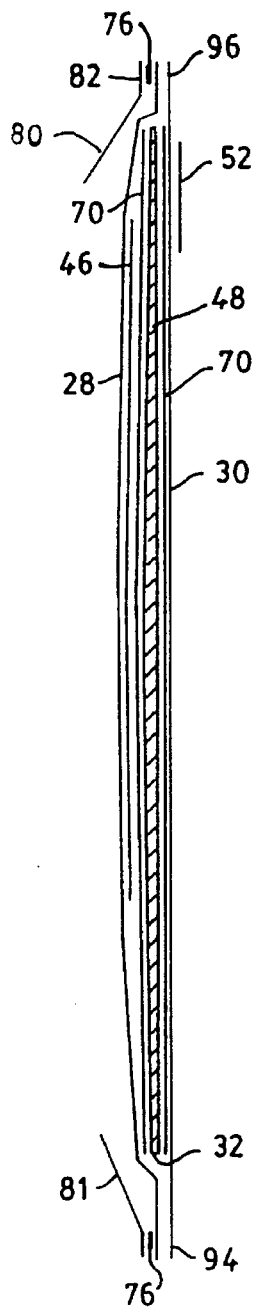
FIG. 6 representatively shows a schematic, cross-sectional view taken along length-wise section 6—6 of the article illustrated in FIG. 4.

With reference to FIGS. 4, 5 and 6, the laterally extending, elasticized bridge flap 80 can be connected to extend over the body-facing surface of the article, and can be constructed to extend laterally beyond the opposed side edge regions 40 of at least one waistband portion, such as the front waistband portion, of the backsheet layer 30. As representatively shown, the appointed waistband section of the article can include a pair of laterally opposed, front side panels 56. The front side panels 56 can be elastically extensible at least along the article cross-dimension 24. For example, side panels 56 may be constructed of a stretch bonded laminate or a neck bonded laminate material. The illustrated construction and arrangement also representatively show an embodiment of the invention where a substantial entirety of the bridge flap 80 is constructed of an elastomeric material. For example, the bridge flap can be substantially entirely composed of a stretch bonded laminate (SBL), a neckbonded laminate (NBL), or the like.

The absorbent article representatively shown in FIG. 4 further comprises an elasticized, front side panel member 56 connected to extend laterally from each of a pair of laterally opposed side edge regions, such as edge regions 44, of at least one waistband portion, such as the front waistband portion 12, of backsheet layer 30. The front side panels can operably have various shapes, such as the illustrated rectangular shape. Alternatively, the shape can be trapezoidal, parabolic, semi-elliptical, or the like.

Each of the side panel members 56 has a portion thereof connected to bridge flap 80, and has a longitudinal extending length dimension which is not less than the length dimension 88 of the bridge flap. In particular aspects of the invention, the bridge flap length dimension is not more than about 120% of the length of the side panel 56. Alternatively, the bridge flap length is not more than about 90%, and optionally is not more than about 70% percent of the length of the associated side panel 56. In other aspects of the invention, the length of bridge flap 80 is not less than about 10%, and optionally is not less than about 20% percent of the length dimension of the side panel 56 to provide desired performance.

Each of the front side panel members 56 extends laterally to a location which is laterally outboard of the terminal side edge region 86 of bridge flap 80. In particular aspects of the invention, side panel 56 extends laterally or at least about 10 percent of the lateral width 54 of side panel 56. Alternatively, bridge flap 80 can extend over at least about 60 percent, and optionally at least about 90 percent of the cross-directional width 54 of the side panels.

The representatively shown embodiments of the article of the invention employ article fasteners 36 which have a factory-bond region secured to the back waistband region 14 of the article. Alternative configurations of the invention can have the article fasteners 36 factory bonded to the lateral end portions of the front waistband region 12 of the article. The latter configuration would then have a front-to-back fastening system. The front-to-back fastening system can provide a more effective activation of bridge flap 80. In particular, the front-to-back fastening system exerts a tensile force onto the side end regions 86 of bridge flap 80 and can more efficiently utilize the entire elasticized width of the bridge flap. Some users, however, may find the front-to-back fastening system inconvenient. Accordingly, such users may prefer the more conventional back-to-front fastening system, such as illustrated in the representatively shown embodiments.

When employing the back-to-front fastening system, the effectiveness of bridge flap 80 can be improved by providing a width dimension 90 which is at least about ½ the normal circumference of the waist section of the intended wearer. Thusly configured, the bridge flap member can overlap and desirably extend past each of the two hip points of the wearer. As a result, the lateral end sections 86 of the bridge flap 80 can more effectively be held in frictional engagement against the wearer's hip points and against the contacting portions of back waistband region 14 to hold the elasticized movable edge region 84 in an elastically extended condition. The cooperative engagement between the end sections of the bridge flap and the hip point regions of the wearer can help to hold and maintain the bridge flap member in a stretched condition, and can improve the operational effectiveness of the bridge flap member 80.

With the back-to-front fastening system, the effectiveness of bridge flap 80 can also be improved by employing supplemental bridge flap fasteners 102. With reference to FIGS. 1 and 2, the representatively shown supplemental bridge flap fasteners are located at the side end regions of the front waistband region of backsheet 30. The supplemental fasteners 102 are positioned on an outward facing surface of the backsheet and are arranged to operably connect and fasten to an inner surface of the back waistband portion of the article. The supplemental bridge flap fasteners can, for example, comprise an adhesive fastening mechanism, a mechanical fastening mechanism, a cohesive fastening mechanism or the like, as well as combinations thereof. In particular configurations, supplemental fasteners 102 are provided by a micro-hook type of mechanism. Such microhooks are available from Minnesota Mining and Manufacturing, a business having offices in St. Paul, Minn. In the illustrated embodiments, the micro-hooks are configured to operably attach to the material comprising topsheet 28.

With reference to FIGS. 4 and 5, the representatively shown configuration includes supplemental fasteners 102 located at the laterally distal side end regions 42 of the side panels 56. In particular arrangements, the supplemental fasteners 102 can extend longitudinally along substantially the entire length dimension 50 of the side panel 56. Alternatively, the supplemental fasteners 102 may extend partially along the side panel length. Where the supplemental fastener 102 extends along only a portion of the side panel length 50, it can be desirable to position the supplemental fastener 102 relatively more closely adjacent to the longitudinally outboard edge of the article waistband.

During the use of the various configurations of the invention, the article is placed upon the wearer, and a first fastener tab 36 is secured to an appointed section of the front waistband region 12. The first supplemental bridge flap fastener 102 can then be secured to an inner bodyside surface of the article. After the first fastening tab 36 is secured to the diaper front waistband section, the user typically holds the front waistband in a desired position and applies a selected level of tension to the remaining unattached end of the rear diaper waistband section 14 prior to securing the second fastener tab 36 onto the front waistband region 12 of the article. Once the second fastener tab is secured, the second supplemental bridge flap fastener 102 can be attached to the inner bodyside surface of the article to hold and maintain a desired elastic extension and elastic tension in a selected portion of the bridge flap 80, such as at movable edge 84.

With the embodiment representatively shown in FIG. 4, the bridge flap 80 can have a width dimension of at least about 7.5 cm. Alternatively, the bridge flap member can have a width dimension of at least about 10 cm, and optionally can have a width dimension of at least about 12.5 cm. In other aspects of the invention, bridge flap 80 can have a width dimension 90 which is not more than about 34–38.1 cm. More particularly, the width dimension can be not more than about 37.1 cm. Alternatively, the bridge flap width dimension can be not more than about 34 cm, and optionally can be not more than about 33.3 cm to provide desired performance. Bridge flap 80 can also have a length dimension 88 which is at least about 1.6 cm. Alternatively, the bridge flap length dimension is at least about 2.4 cm, and optionally is at least about 2.5 cm. In further aspects of the invention, the bridge flap 80 has a length dimension which is not more than about 8–12.7 cm. More particularly the length dimension can be not more than about 10 cm. Alternatively, the bridge flap length dimension is not more than about 8 cm, and optionally is not more than about 7.5 cm to provide desired performance.

With regard to an adult-sized article similar to the embodiment representatively shown in FIG. 4, the bridge flap 80 can have a width dimension of at least about 25.4 cm. Alternatively, the bridge flap member can have a width dimension of at least about 30.5 cm, and optionally can have a width dimension of at least about 35.5 cm. In other aspects of the adult-sized article, the bridge flap 80 can have a width dimension 90 which is not more than about 89 cm. Alternatively, the bridge flap width dimension can be not more than about 76 cm, and optionally can be not more than about 63.5 cm to provide desired performance. The bridge flap 80 can also have a length dimension 88 which is at least about 2.5 cm. Alternatively, the bridge flap length dimension is at least about 3.8 cm, and optionally is at least about 5 cm. In further aspects of the invention, the bridge flap 80 has a length dimension which is not more than about 15.5 cm. Alternatively, the bridge flap length dimension is not more than about 12.7 cm, and optionally is not more than about 10.2 cm to provide desired performance.

As illustrated in FIG. 4, a particular aspect of the invention can include elasticized fastener panels 100 attached at the back waistband section 14 of the article. Accordingly, when the fastener panels 100 are pulled and tensioned to secure the fastener tabs 36 and fit the article on the wearer, the tension can be transmitted to at least a portion of the bridge flap 80 to help stretch the bridge flap. Due to the bridge flap construction, the stretching operation causes a displacement of the bridge flap movable edge 84 which urges the movable edge into an operable contact against the wearer's body. This can bridge any spacing distance that might occur between the topsheet 28 and the wearer's skin, and can form an effective pocket capable of trapping any free-flowing liquid. The trapped liquid can then be more effectively absorbed by the retention portion of the absorbent structure.

FIGS. 4 and 6 also representatively show a configuration having a supplemental, rear bridge flap member 81 connected to the rear waistband portion of the diaper. The construction of the rear bridge flap can be the same as or similar to the construction of the primary, front bridge flap member 80. In addition, the attachments of the rear flap 81 to the diaper can be the same as or similar to the attachments described with respect to the front bridge flap 80. For example, the longitudinally outboard edge of rear flap 81 can be substantially fixed to the diaper with attachments 76, the lateral side regions of the rear flap 81 can be substantially fixed to the laterally opposed pair of rear fastener panels 100 or topsheet 28 with side attachments 98, and the longitudinally inboard edge of rear flap 81 can be movable and operably elasticized, in accordance with the arrangements described herein. Accordingly, when the fastener panels 100 are pulled and tensioned to secure the fastener tabs 36 and fit the article on the wearer, the tension can be transmitted to at least a portion of the rear bridge flap 81 to help stretch the rear bridge flap. Due to the construction of the rear bridge flap, the stretching operation causes a displacement of the movable edge of the rear bridge flap 81 which urges the movable edge into an operable contact against the wearer's body. This can bridge any spacing distance that might occur between the topsheet 28 and the wearer's skin, and can form an effective rear pocket capable of trapping any free-flowing liquid at the back waistband region of the article.

In the various configurations of the invention, it has been found that proper positionings of the article fastening means and the bridge flap member can be important to the operation of the bridge flap member 80. With reference to FIG. 1, for example, a longitudinally terminal edge of the user bond region of fastener tab 36 is spaced from the longitudinally terminal edge of article 10 by a first discrete distance 118. With reference to the opposite end of the article, the movable edge region 84 of bridge flap 80 is spaced from the opposite, longitudinally terminal edge of the article by a second discrete distance 120. To provide desired performance, distance 118 should be less than distance 120. If distance 118 is too large, the use of fastener tabs 36 may undesirably interfere with the operation of bridge flap 80. In particular, the fastener tabs, when employed to secure the article on the wearer, can excessively interfere with the desired retraction of the bridge flap movable edge.

In particular aspects of the invention, there can be a stretch differential between the fixed edge region 82 and the movable edge region 84 of the bridge flap. When the article is in its contracted and gathered condition, the amount of elasticized extensibility of the movable edge region 84 is relatively greater than the amount of elasticized extensibility of fixed edge region 82. The degree of elasticized gathering of the movable edge region 84 should be sufficient to operably direct the movable edge region away from topsheet 28 to produce a spanning, bridge-like configuration which can maintain the movable edge region in a substantially continuous contact with the wearer's body. The elasticization, however, should be regulated and limited to avoid excessive curling in of the lateral ends of the article. Such curling can interfere with the desired operation of the bridge flap, and can make the article more difficult to apply onto the wearer's body.

The differential in extensibility between fixed edge region 82 and movable edge region 84 can be provided by various techniques and structures. For example, the elastic members at movable edge region 84 may have a greater cross-directional extent than the elastics located at fixed edge region 82. Alternatively, a different type of elastomeric material having a lower level of extensibility may be located at the fixed edge region 82 of the bridge flap 80. Optionally, stiffening members may be employed to restrict the extensibility at the fixed edge region 82.

Where the configuration of the invention incorporates containment flaps 62, the bridge flap 80 is desirably configured to overlie a body-facing surface of the containment flaps. Accordingly, the bridge flap is superposed over the containment flaps and can be positioned between the containment flaps and the wearer's body. Thusly arranged, the bridge flap can more effectively bridge across any gaps between topsheet 28 and the wearer's body, and can more effectively maintain a substantially continuous contact against the wearer. In further aspects of the invention, the bridge flap movable edge 84 is substantially independent of and substantially unsecured to the containment flaps. More particularly, the movable edge is substantially unsecured to the containment flap movable edges 66. As a result, the extensibility and contractibility of the bridge flap movable edge 84 is substantially unrestricted by the containment flaps, and the bridge flap can provide a more independent and effective bridging operation.

Bridge flap 80 is desirably assembled into the article while the bridge flap is in an elastically contractible condition. For example, suitable techniques for assembling the bridge flap into the article include applying and attaching a prestretched bridge flap onto the topsheet 28. Alternatively, the bridge flap 80 may be composed of a heat-shrinkable, or otherwise heat activatable material. After securement to the desired portion of topsheet 28, the bridge flap material can be activated to elastically contract the bridge flap along its lateral width dimension.

The bridge flap movable edge region 84 is desirably configured to bridge a distance of at least about 0.5 cm. Alternatively, the movable edge region can bridge a distance of at least about 1 cm. In other configurations, the movable edge region 84 can bridge a distance of up to about 8 cm, and optionally can bridge a distance of up to about 10 cm to provide improved performance.

With reference to FIG. 7, a further aspect of the invention can provide an absorbent article having at least one elasticized side panel 58 connected to a lateral end region 40 of the back waistband portion 14 of the article. The side panel 58 is constructed for interconnecting with a cooperating section of the article to thereby form an assembled bridge flap 180 (e.g. FIG. 8) which extends about a wearer and is arranged to provide a bodyside surface for contacting the wearer's body. The cooperating section of the side panel 58 includes fastening means, such as provided by fasteners 74, for securing each of the side panels 58 about the wearer. In addition, the article includes waistband fastening means, such as provided by fasteners 36, for securing the article front waistband portion to the article back waistband portion to thereby encircle the wearer with the waistband portions. The article also includes a waistband-edge attaching means 112 for securing a laterally extending, longitudinally outboard waistband edge of the assembled bridge flap to an appointed, cooperating section of the front waistband portion of the article. In particular configurations, the absorbent article can optionally have a pair of elasticized side panels 58 connected at laterally opposed end regions of the back waistband portion of the article, and each of the side panels can include a portion of the waistband-edge attaching means 112.

In the illustrated embodiment, the waistband fasteners 36 have their factory-bond sections connected to the front waistband region of the article, and are arranged to have their user-bond sections connect to the back waistband region of the article during use. Optionally, the fasteners 36 can have their factory-bond sections connected to the back waistband region of the article, and can be arranged to have their user-bond sections connect to the front waistband region of the article during use. In further configurations, the fasteners 36 can be operably connected to intermediate fastener panels. For example, elasticized fastener panels 100 can be connected to the fasteners 36 in the arrangement illustrated in FIG. 4.

The attaching means 112 can be composed of an adhesive attachment, a cohesive attachment, an interlocking mechanical attachment or the like, as well as combinations thereof. The waistband-edge attaching means is configured to operably connect with a cooperating section, such as an inward bodyside surface of the article, which is located along and/or proximate a longitudinally terminal edge of the front waistband region 12 of the article. Where a cohesive or mechanical attaching mechanism is employed, a cooperating element of the attaching mechanism can be operably secured to an appointed article section, such as a bodyside surface of topsheet 28. Desirably, the resultant waistband-edge attachment can provide a liquid-resistant seal which can effectively block the escape of liquid and thereby help to reduce leakage.

With reference to FIG. 7A, yet another aspect of the invention can include at least one elasticized rear side panel 58 which connects at an end region 40 of the back waistband portion 14 of the article, and includes a foldable section 60 which can be folded longitudinally along a laterally extending fold line. Alternative configurations of the invention can include a pair of elasticized rear side panels 58 which are connected at laterally opposed end regions 40 of the back waistband portion 14 of the article. Where a pair of side panels 58 are employed, the side panels may be unequal in size or may be substantially equal in size.

The representatively shown embodiment of FIG. 7A incorporates an asymmetric arrangement having a relatively large side panel 58 configured to wrap around the front of the wearer's torso. The side panel 58 includes the foldable section 60 which extends length-wise past a longitudinally terminal edge 94 of the backsheet layer 30. In the illustrated embodiment, a second relatively smaller side panel 58 does not include a foldable section 60. The shown, relatively smaller side panel 58, however, does include a pair of flap fasteners 74 factory bonded to a laterally terminal end region of the side panel. The illustrated fasteners 74 are shown in a folded over storage condition against an inner bodyside surface of the smaller side panel 58. In arrangements having a pair of laterally opposed side panels 58, it should be appreciated that both of the side panels 58 can include the extending foldable section 60.

Each rear side panel 58 can include a foldable section 60 which extends laterally along at least about 50% of the width-wise extent of the rear side panel. Alternatively, the foldable section extends at least about 75%, and optionally about 100% of the width-wise extent of the rear side panel 58. In the illustrated embodiment the foldable section 60 extends laterally along at least about 100% of the width-wise extent of the rear side panel 58. The foldable section also extends longitudinally past a longitudinally terminal edge 94 of the backsheet layer 30 by a border distance 114 of at least about 1 cm. Alternatively, the border distance is at least about 1.3 cm to provide improved performance. In other aspects of the invention, border distance 114 can measure up to about 3.8 cm. Alternatively, the border distance can measure up to about 5.7 cm to provide desired benefits.

In the various configurations represented by FIG. 7A, the waistband-edge attaching means can be configured to provide a suitable fold attachment means 104. The fold attachments 104 can be constructed to hold the foldable sections 60 of the side panels 58 in a substantially C-folded condition which substantially wraps about a laterally extending, terminal edge 96 of the article front waistband portion 12. Accordingly, the fold attachments 104 can operably connect to an appointed section of the outerside surface of the article. The appointed section can typically extend laterally along and proximate to the terminal edge of the front waistband portion. Alternative arrangements of the invention can include a combination of the internal waistband-edge attaching means 112 and the fold attachments 104.

With reference to FIGS. 8–11, the rear side panels 58 are constructed for interconnecting with each other about a wearer's body to thereby form an assembled bridge flap 180, which is arranged to provide a bodyside surface for contacting the wearer. A securing means, such as flap fasteners 74 can be employed to form the assembled bridge flap. The flap fasteners can be constructed of any suitable fastening mechanism, such as an adhesive fastening mechanism, a mechanical fastening mechanism, a cohesive fastening mechanism or the like, as well as combinations thereof.

Materials suitable for constructing the various configurations of rear side panels 58 can be the same as or similar to the materials employed to construct front side panels 56 and bridge flap 80. Accordingly, the rear side panels 58 can be elasticized by constructing the rear side panels of an elastic material, such as an elastic laminate, which is stretchable along a lateral cross-direction of the article and operably elasticizes a substantial entirety of the side panel surface area. Alternatively, the rear side panel 58 can be elasticized by connecting at least one separate elastic member, in an elastically contractible condition, to the rear side panel in constructions similar to those previously discussed.

In infant or child-sized articles, the assembled bridge flap 180 has an assembled width dimension of at least about 7.6 cm. Alternatively, the assembled bridge flap has an assembled width dimension of at least about 10 cm, and optionally has an assembled width dimension of at least about 12.7 cm. In addition, the assembled bridge flap can have an assembled width dimension of not more than about 26–36.8 cm. More particularly, the assembled width dimension can be not more than about 30.5 cm. Alternatively, the assembled width dimension can be not more than about 26 cm, and optionally can be not more than about 24 cm to provide desired benefits. In other aspects of the invention, assembled bridge flap 180 has an assembled length dimension 88 which is at least about 1.9 cm. Alternatively, the assembled length of the bridge flap 180 is at least about 2.5 cm, and optionally, is at least about 3 cm to provide desired performance. Assembled bridge flap 180 can also have an assembled length dimension which is not more than about 8.5–12.7 cm for the child or infant sized articles. More particularly, the assembled length dimension can be not more than about 10.2 cm. Alternatively, the length dimension is not more than about 8.5 cm, and optionally is not more than about 7.7 cm to provide desired benefits.

In an adult-sized article, assembled bridge flap 180 can have an assembled width dimension of at least about 30.5 cm. Alternatively, the assembled bridge flap has an assembled width dimension of at least about 45.7 cm, and optionally has an assembled width dimension of at least about 50.8 cm. In addition, the assembled bridge flap of the adult-sized article can have an assembled width dimension of not more than about 101.6 cm. Alternatively, the assembled width dimension can be not more than about 89 cm, and optionally can be not more than about 76.2 cm to provide desired benefits. In other aspects of the adult-sized article, assembled bridge flap 180 can have an assembled length dimension 88 which is at least about 7.6 cm. Alternatively, the assembled length of the bridge flap 180 is at least about 10 cm, and optionally, is at least about 11 cm to provide desired performance. The adult-sized assembled bridge flap 180 can also have an assembled length dimension which is not more than about 23 cm for the adult-sized articles. Alternatively, the length dimension is not more than about 16 cm, and optionally is not more than about 15.2 cm to provide desired benefits.

Figure 9:
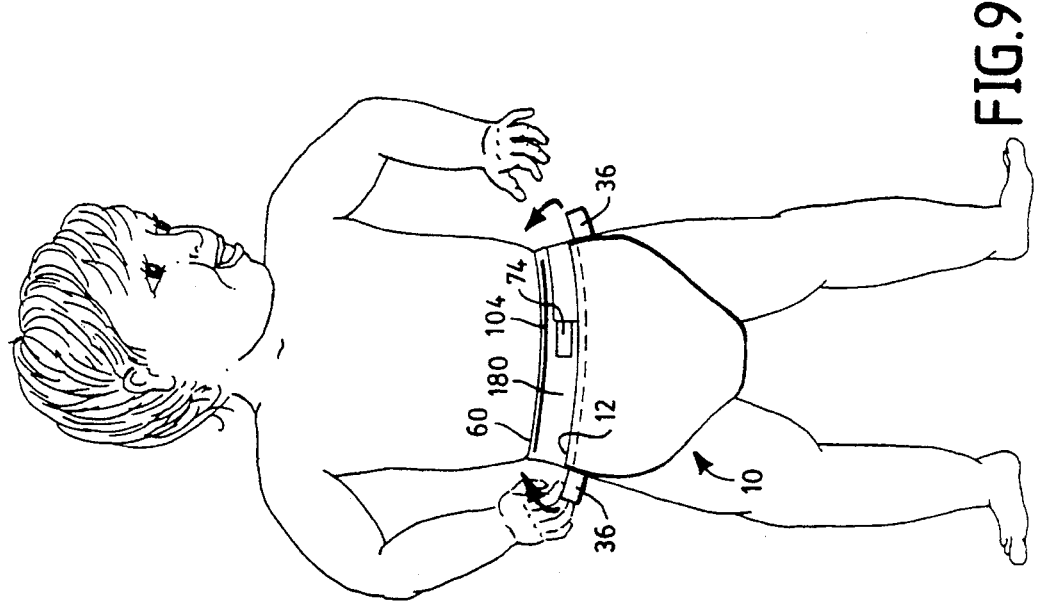
FIG. 9 representatively shows a view of the article of FIG. 8, wherein a front waistband portion of the article has been secured about the wearer's body.
Figure 10:
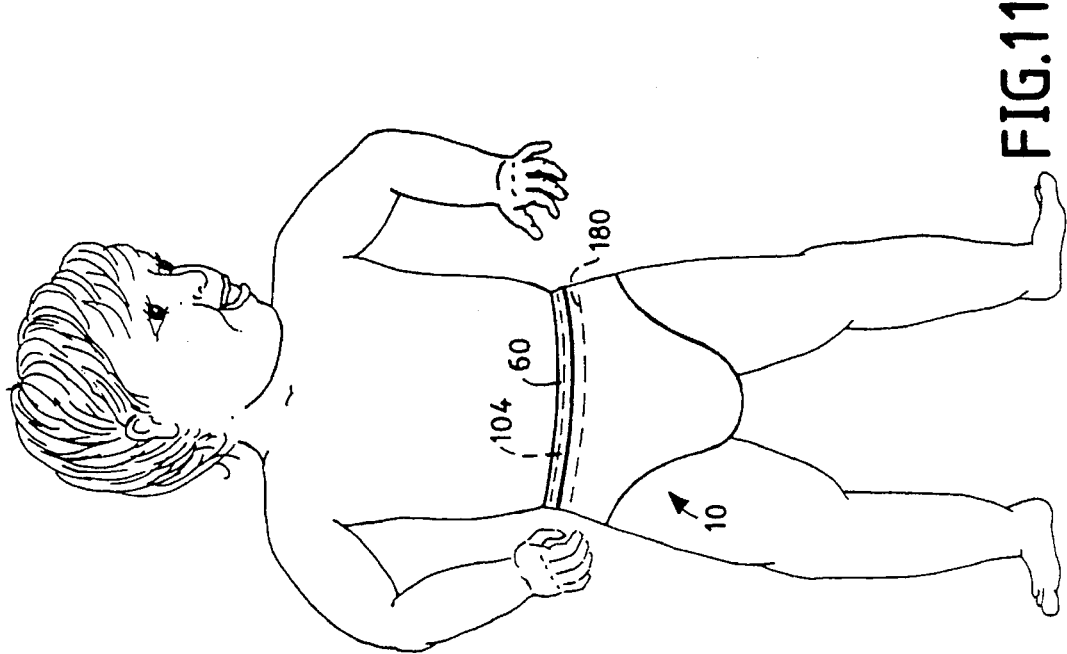
FIG. 10 representatively shows a view of the article of FIG. 8, wherein the foldable sections of the side panels are being folded about a waistband edge of the article.
Figure 11:
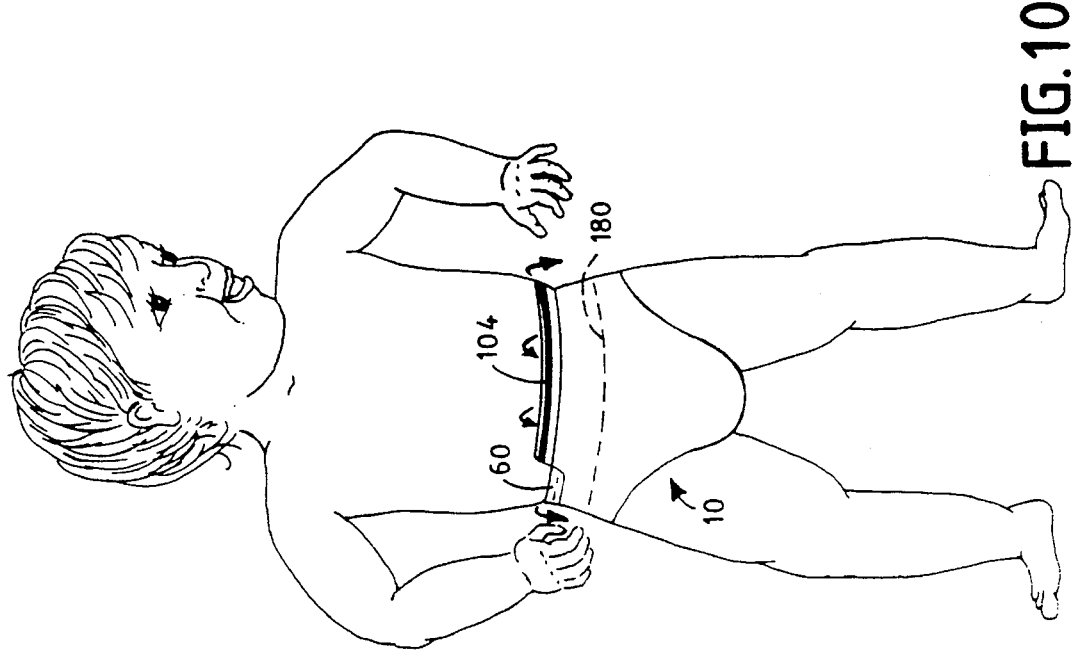
FIG. 11 representatively shows a view of the article of FIG. 8, wherein the foldable sections of the side panels have been folded about a waistband edge of the article.

The article fastening means, such as provided by fastener tabs 36, can secure the article front waistband portion 12 to the article back waistband portion 14 to thereby encircle the wearer with the article waistband portions (FIG. 9.). The extending foldable sections 60 can then be wrapped around a laterally extending, terminal edge 96 of the article front waistband portion 12 into a substantially C-folded condition (FIGS. 10 and 11). An additional attaching means, such as fold attachments 104, can be employed to hold the foldable sections 60 of the side panels 58 in the C-folded condition. The fold attachments 104 can be provided by any suitable attaching mechanism, such as adhesives, cohesives, snaps, hooks, VELCRO® fasteners and the like, as well as combinations thereof. As a result, the assembled bridge flap 180 and the cooperating foldable sections 60 can provide a more secure conformity to the wearer's body, and can provide a more effective seal against the leakage of liquid. The bridge flap is capable of spanning across any gaps that may develop between the wearer's body and the front panel of the diaper. As a result, liquid can be more effectively held inside the diaper, and the absorbent structure has more time in which to absorb the liquid. In addition, the relatively wide bridge flap 180 can wrap around a greater proportion of the wearer's body to help support the front panel of the diaper and to reduce the tendency to droop at the diaper front panel.

In the various configurations of the invention, the side panels 56 and 58 and/or the fastener panels 100 can comprise a substantially nonwettable material, which may be fibrous. The nonwettable characteristic can help reduce undesired movement or wicking of liquids along the surfaces of the panels.

In the various configurations of the invention, the bridge flap 80 (or 180) can be constructed and arranged to overlie selected longitudinal end sections 78 of the absorbent structure, such as the longitudinal end regions of retention portion 48. As a result, the bridge flap can more effectively reduce leakage and a laterally extending, substantially liquid impermeable, sealing attachment 76 can block the flow of liquid.

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article having a front waistband portion, a back waistband portion and an intermediate portion which interconnects said front and back waistband portions, said article comprising:

a backsheet layer;

an absorbent retention portion superposed on said backsheet layer;

a liquid permeable topsheet layer superposed on said retention portion and connected to sandwich said retention portion between said topsheet and backsheet layers;

a laterally extending, elasticized bridge flap connected to extend over a body-facing surface of said article and constructed to extend laterally beyond opposed side edge regions of at least one waistband portion of said backsheet layer, said bridge flap having a laterally extending, substantially fixed edge region attached to said at least one waistband portion of said article and having a laterally extending, movable edge region positioned longitudinally inboard of said substantially fixed edge region; and an elasticized panel member directly connected to each side edge region of said at least one waistband portion of said backsheet layer and extending laterally therefrom, each said elasticized panel member having a portion thereof which is laterally outward of said waistband side edge region and is connected to said bridge flap at a bridge flap portion located laterally outward of said waistband side edge region to stretch said bridge flap when said panel members are tensioned, and having a longitudinally extending length dimension which is not less than a length dimension of said bridge flap.

2. An absorbent article as recited in claim 1, wherein said bridge flap has a longitudinally extending length dimension of not less than about 4 cm.

3. An absorbent article as recited in claim 2, wherein said bridge flap is connected to a front waistband portion of said article.

4. An absorbent article as recited in claim 1, wherein said edge flap has a longitudinally extending length dimension which is not more than about 120% of a length dimension of said side panel member.

5. An absorbent article as recited in claim 1, wherein said longitudinally extending length dimension of said bridge flap is not more than about 70% of said length dimension of said side panel member.

6. An absorbent article as recited in claim 1, wherein said side panel members extend laterally to locations which are laterally outboard of terminal side edge regions of said bridge flap.

7. An absorbent article as defined in claim 1, further comprising a pair of laterally opposed supplemental fasteners attached to an outward facing surface of said article at said front waistband portion of said backsheet, said supplemental fasteners configured for maintaining a desired elastic tension in a selected portion of said bridge flap.

8. An absorbent article as recited in claim 7, further comprising attaching means for securing side edge regions of said bridge flap to provide liquid-resistant seals between said bridge flap and said side panel members.

9. An absorbent article as recited in claim 1, wherein said bridge flap has a flap surface area and is elasticized by constructing said flap of an elastomeric material to elasticize a substantial entirety of said flap surface area.

10. An absorbent article as recited in claim 1, wherein said bridge flap has a flap surface area and is elasticized by connecting at least one separate elastic member to said bridge flap to elasticize a selected strip region of said flap surface area.

11. An absorbent article as recited in claim 1, wherein said bridge flap is composed of a substantially nonwettable material which is permeable to a movement of gas therein.

12. An absorbent article as recited in claim 1, wherein said bridge flap is composed of a material which is resistant to a passage of liquid through a thickness thereof.

13. An absorbent article as recited in claim 1, further comprising at least a pair of laterally spaced-apart, longitudinally extending, elasticized containment flaps attached to a body-facing surface of said article; wherein said bridge flap is arranged to overlie said containment flaps and said topsheet layer to provide a bodyside surface for contacting a wearer's body, and wherein said bridge flap movable edge is substantially unattached to said containment flaps.

14. An absorbent article as recited in claim 1, wherein said bridge flap fixed edge is elasticized with a first elastic member, and said bridge flap movable edge is elasticized with a second elastic member to provide for a differential elasticized extensibility between said substantially fixed edge region and said movable edge region of said bridge flap, with said substantially fixed edge region having a relatively lower elasticized extensibility.

15. An absorbent article as recited in claim 1, wherein said bridge flap movable edge region has an elasticized, lateral retractability of at least about 10%, as determined with respect to its contracted gathered width, and having an elastic tension within the range of about 40–150 gm-force, as determined when said movable edge region is extended to a flat-out configuration of said bridge flap.

16. An absorbent article as recited in claim 1, wherein said bridge flap is connected to a back waistband portion of said article.

17. An absorbent article as recited in claim 16, wherein each of said panel members comprises an elasticized fastener panel, and a fastener tab is attached to each fastener panel.

18. An absorbent article as recited in claim 17, further comprising a second, laterally extending, elasticized bridge flap connected to extend over an appointed body-facing surface of a front waistband portion said article and constructed to extend laterally beyond opposed side edge regions of a front waistband portion said backsheet layer, said second bridge flap having a laterally extending, substantially fixed edge region attached to said front waistband portion of said article and having a laterally extending, movable edge region positioned longitudinally inboard of said substantially fixed edge region of the second bridge flap.

19. An absorbent article as recited in claim 18, further comprising an elasticized front panel member connected to extend laterally from each of said side edge regions of said front waistband portion of said backsheet layer, said front panel member having a portion thereof connected to said second bridge flap to stretch said second bridge flap when said front panel members are tensioned, and having a longitudinally extending length dimension which is not less than a length dimension of said bridge flap.

* * * * *